(12) United States Patent
Thalacker et al.

(10) Patent No.: US 11,612,548 B2
(45) Date of Patent: Mar. 28, 2023

(54) RADIOPAQUE DENTAL COMPOSITION

(71) Applicant: 3M INNOVATIVE PROPERTIES COMPANY, St. Paul, MN (US)

(72) Inventors: Christoph H. Thalacker, Weilheim (DE); Adrian S. Eckert, Herrsching (DE); Henry Loll, Gilching (DE); Karsten Dede, Landsberg (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 319 days.

(21) Appl. No.: 16/762,172

(22) PCT Filed: Nov. 5, 2018

(86) PCT No.: PCT/IB2018/058674
§ 371 (c)(1),
(2) Date: May 7, 2020

(87) PCT Pub. No.: WO2019/092580
PCT Pub. Date: May 16, 2019

(65) Prior Publication Data
US 2020/0360240 A1    Nov. 19, 2020

(30) Foreign Application Priority Data
Nov. 8, 2017  (EP) .................................... 17200519

(51) Int. Cl.
| | | |
|---|---|---|
| A61K 6/30 | (2020.01) | |
| A61C 5/30 | (2017.01) | |
| A61K 6/40 | (2020.01) | |
| A61C 13/00 | (2006.01) | |
| A61K 49/04 | (2006.01) | |

(52) U.S. Cl.
CPC .................. A61K 6/30 (2020.01); A61C 5/30 (2017.02); A61C 13/0007 (2013.01); A61C 13/0022 (2013.01); A61K 6/40 (2020.01); A61K 49/04 (2013.01); *A61C 2201/005* (2013.01)

(58) Field of Classification Search
CPC ...................................................... A61K 6/30
See application file for complete search history.

(56) References Cited

U.S. PATENT DOCUMENTS

| | | | |
|---|---|---|---|
| 4,119,610 | A | 10/1978 | Kaelble |
| 4,259,075 | A | 3/1981 | Yamauchi |
| 4,369,298 | A | 1/1983 | Kida |
| 4,499,251 | A | 2/1985 | Omura |
| 4,503,169 | A | 3/1985 | Randklev |
| 4,537,940 | A | 8/1985 | Omura |
| 4,539,382 | A | 9/1985 | Omura |
| 4,642,126 | A | 2/1987 | Zador |
| 4,652,274 | A | 3/1987 | Boettcher |
| 4,695,251 | A | 9/1987 | Randklev |
| 4,696,955 | A | 9/1987 | Kuhlmann |
| 4,795,823 | A | 1/1989 | Schmitt |
| 4,798,536 | A | 1/1989 | Katz |
| 4,872,936 | A | 10/1989 | Engelbrecht |
| 5,130,347 | A | 7/1992 | Mitra |
| 5,530,038 | A | 6/1996 | Yamamoto |
| 5,996,796 | A | 12/1999 | Kvitrud |
| 5,998,495 | A | 12/1999 | Oxman |
| 6,025,406 | A | 2/2000 | Oxman |
| 6,043,295 | A | 3/2000 | Oxman |
| 6,084,004 | A | 7/2000 | Weinman |
| 6,105,761 | A | 8/2000 | Peuker |
| 6,187,833 | B1 | 2/2001 | Oxman |
| 6,387,981 | B1 | 5/2002 | Zhang |
| 6,444,725 | B1 | 9/2002 | Trom |
| 6,458,868 | B1 | 10/2002 | Okada |
| 6,572,693 | B1 | 6/2003 | Wu |
| 6,730,156 | B1 | 5/2004 | Windisch |
| 6,765,036 | B2 | 7/2004 | Dede |
| 6,899,948 | B2 | 5/2005 | Zhang |
| 7,968,617 | B2 | 6/2011 | Thalacker |
| 8,183,305 | B2 | 5/2012 | Neffgen |
| 9,675,529 | B2 | 6/2017 | Abuelyaman |
| 2004/0206932 | A1 | 10/2004 | Abuelyaman |
| 2005/0252413 | A1 | 11/2005 | Kangas |
| 2005/0252414 | A1 | 11/2005 | Craig |
| 2005/0256223 | A1 | 11/2005 | Kolb |
| 2009/0298966 | A1 | 12/2009 | Vanini |
| 2015/0374465 | A1 | 12/2015 | Bürke |

FOREIGN PATENT DOCUMENTS

| | | | | |
|---|---|---|---|---|
| DE | 4419386 A1 | * | 12/1995 | ............ A61K 6/887 |
| EP | 0712622 | | 5/1996 | |
| EP | 1051961 | | 11/2000 | |
| GB | 2181144 | | 4/1987 | |
| JP | H0848729 A | * | 2/1996 | |

(Continued)

OTHER PUBLICATIONS

Kumar, "Bromination of Aromatic Compounds Using Ammonium Bromide and Oxone", Synthesis, 2010, vol. 10, pp. 1629-1632.
Moszner, "New developments of polymeric dental composites", Progress in Polymeric Science, 2001, vol. 26, pp. 535-576.
Tauscher, "New Radiopaque Bromine-Containing Monomers for Dental Restorative Materials", Macromolecular Materials and Engineering, 2016, vol. 301, pp. 733-742.
International Search Report for PCT International Application No. PCT/IB2018/058674, dated Jan. 7, 2019, 5 pages.

*Primary Examiner* — Michael F Pepitone
(74) *Attorney, Agent, or Firm* — 3M Innovative Properties Company

(57) ABSTRACT

The invention relates to a radiation-curable radiopaque dental composition comprising a resin matrix comprising cross-linkable component(s) as Component A, ethylenically unsaturated component(s) with acidic moiety as Component B, an initiator system comprising photoinitiator(s) as Component C, reducing agent(s) as Component D, Component A containing at least two (meth)acrylate moieties and a brominated aromatic moiety selected from brominated resorcinol, catechol, tyrosol, benzoic acid, or phenol moieties. The composition can be used for producing an x-ray visible dental adhesive composition, restoration primer or dental sealant.

20 Claims, No Drawings

(56) References Cited

FOREIGN PATENT DOCUMENTS

| WO | WO 2003-063804 | 8/2003 |
| WO | WO 2011-056814 | 5/2011 |
| WO | WO 2012-125885 | 9/2012 |
| WO | WO 2015-126865 | 8/2015 |

* cited by examiner

RADIOPAQUE DENTAL COMPOSITION

CROSS REFERENCE TO RELATED APPLICATIONS

This application is a national stage filing under 35 U.S.C. 371 of PCT/IB2018/058674, filed 5 Nov. 2018, which claims the benefit of European Application No. 17200519.1, filed 8 Nov. 2017, the disclosures of each of which are incorporated by reference herein in their entireties.

FIELD OF THE INVENTION

The invention relates to a radiation-curable, radiopaque dental composition, in particular a radiation-curable dental adhesive composition comprising brominated radiation-curable components comprising an aromatic moiety, in particular a brominated resorcinol, catechol, tyrosol, benzoic acid, or phenol moiety.

BACKGROUND

In order to be able to detect secondary caries, dental compositions, in particular dental compositions used for restorative purposes should be x-ray opaque to a certain degree.

X-ray opacity can generally be obtained by either incorporating x-ray opaque fillers into the polymerizable resin or by using x-ray opaque monomers. Traditionally, radiopacity is provided by using inorganic fillers containing heavy atoms.

Commercially available radiopaque adhesives are based on fillers like ground barium glass, e.g. Optibone™ FL (Kerr). These fillers can settle out of the adhesive formulation under the influence of gravity. This can make the adhesive inhomogeneous and may require shaking of the bottle before the application of the adhesive.

The use of brominated monomers for achieving radiopacity has been suggested e.g. N. Moszner, U. Salz: "New developments of polymeric dental composites", Prog. Polym. Sci. 2001, 26, 535-576, or S. Tauscher, Y. Catel, R. Liska, N. Moszner: "New Radiopaque Bromine-Containing Monomers for Dental Restorative Materials", Macromol. Mater. Eng. 2016, 301, 733-742. The radiopaque monomers are synthesized from pentaerythritol tribromide and 2,2,2-tribromethanol. It is outlined that the bromine atoms have an impact on the reactivity and that some brominated monomers are more reactive than others.

U.S. Pat. No. 4,119,610 (Kaelble) describes a brominated acrylate dental composition which can be used as a dental restorative or pit and fissure sealant having improved environmental resistance. The diacrylates are symmetrical compounds having a central brominated aryl amine nucleous providing hydrophobicity and desirable polar properties.

U.S. Pat. No. 4,696,955 (Kuhlmann) describes an x-ray opaque dental restoration material containing a brominated aromatic di-methacrylic ester component.

U.S. Pat. No. 8,183,305 B2 (Neffgen et al.) describes a radiopaque infiltrant containing a radiopaque nanoscale filler and/or radiopaque organic compounds. As radiopaque organic compounds triphenylbismuth derivatives and iodine-substituted benzoic esters are mentioned. WO 2015/126865 A1 (3M) describes an adhesive bonding composition and use thereof.

U.S. Pat. No. 9,675,529 B2 (Abuelyman et al.) relates to a curable dental composition comprising at least one dental resin comprising at least two ethylenically unsaturated groups, a high refractive index monomer, an addition fragmentation agent and optionally an inorganic oxide filler.

However, none of the solutions outlined in these references is completely satisfying, in particular, if the respective dental composition should be an adhesive composition.

SUMMARY OF INVENTION

There is still a need for an improved dental composition which can be used for adhesively fixing dental restorations to dental surfaces.

The dental composition should be sufficiently storage stable, radiopaque, low viscous and enable a sufficiently high bond strength to dental surfaces.

Ideally, the dental composition can also be applied by using a delivery device having a nozzle with a small diameter.

The dental composition described in the present text and claims is suitable to address this need.

In one embodiment the present invention features a dental composition comprising
a resin matrix comprising:
cross-linkable component(s) as Component A,
ethylenically unsaturated component(s) with acidic moiety as Component B,
an initiator system comprising
photoinitiator(s) as Component C,
reducing agent(s) as Component D,
Component A comprising a brominated aromatic moiety, in particular a brominated resorcinol, catechol, tyrosol, benzoic acid, or phenol moiety.
In particular, polymerizable monomer(s) according to formula (I) were found to be useful as Component (A):

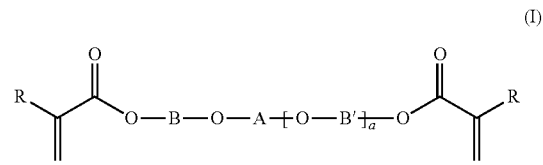

with:
B—O-A-[-O—B'—]$_a$ representing the monomer backbone as linkage between the reactive (meth)acrylate moieties,
a=0 or 1,
A being selected from:

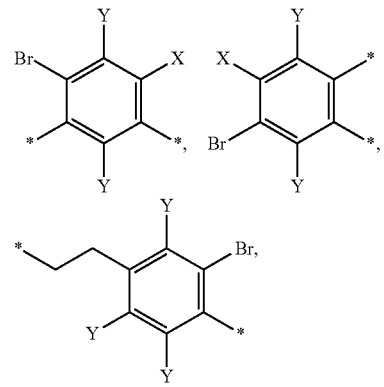

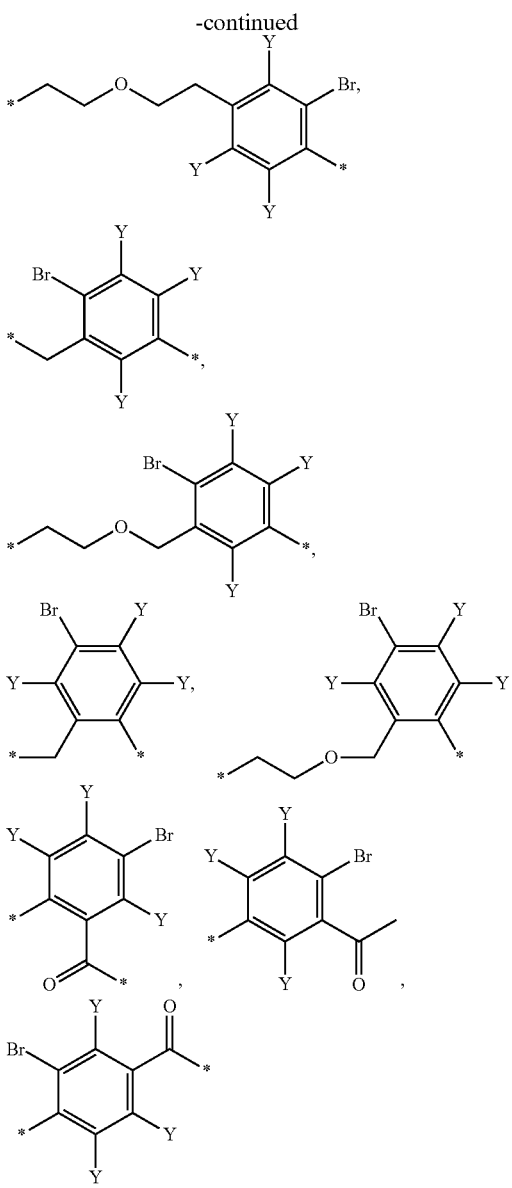

A being always attached as aryl-alkyl ether onto B and/or B',

B being selected from:

\*—(CH$_2$)$_b$—\*, \*—(CH$_2$—CH$_2$—O—CH$_2$—CH$_2$)—\*, \*—(CH$_2$—CH$_2$—O—CH$_2$—CH$_2$—CH$_2$)—\*, \*—(CH$_2$—CH$_2$—CH$_2$—O—CH$_2$—CH$_2$—CH$_2$)-\*,

B being always attached as alkyl ester onto the (meth) acrylate reactive moiety, b=2 to 6, B' being selected from \*—(CH$_2$)$_{b'}$—\*, \*—(CH$_2$—CH$_2$—O—CH$_2$—CH$_2$)—\*, B' being always attached as alkyl ester onto the (meth) acrylate reactive moiety, b'=2 to 6, R=H, methyl, X being selected from H, methyl, ethyl, hexyl, tert-butyl, Br, Y=H, Br, "\*" representing those site(s) of a moiety of the monomer, where that moiety is bonded to another moiety of the monomer.

as described in the present text and the claims.

The dental composition is in particular for use in a process comprising the step of treating the surface of a dental restoration and/or treating a dental surface (e.g. enamel, dentin), the process comprising the step of applying the dental composition as described in any of the preceding claims to the surface of a dental restoration or a dental surface as described in the present text and the claims.

In another embodiment, the invention relates to a process of producing the dental composition by a mixing the respective components as described in the present text and the claims.

A further embodiment of the invention is directed to a kit of parts comprising the dental composition as described in the claims and the present text and either of the following parts alone or in combination: dental filling material, dental milling blank, dental cement, hydrofluoric acid etchant, sandblasting medium, sandblasting device, a dental filling material.

The invention is also related to the use of the monomer containing a brominated aromatic moiety, in particular a brominated resorcinol, catechol, tyrosol, benzoic acid, or phenol moiety as described in the present text and the claims for producing a homogeneous, x-ray visible dental adhesive composition, restoration primer or dental sealant.

Unless defined differently, for this description the following terms shall have the given meaning:

The term "compound" or "component" is a chemical substance which has a particular molecular identity or is made of a mixture of such substances, e.g., polymeric substances.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

A "dental composition" or a "composition for dental use" or a "composition to be used in the dental field" is any composition which can and is to be used in the dental field. In this respect the composition should be not detrimental to the patients' health and thus free of hazardous and toxic components being able to migrate out of the composition.

Dental compositions are typically hardenable compositions, which can be hardened at ambient conditions, including a temperature range of 15 to 50° C. or 20 to 40° C. within a time frame of 30 min or 20 min or 10 min. Higher temperatures are not recommended as they might cause pain to the patient and may be detrimental to the patient's health.

Dental compositions are typically provided to the practitioner in rather small volumes, that is volumes in the range of 0.1 to 100 ml or 0.5 to 50 ml or 1 to 30 ml. Thus, the storage volume of useful packaging devices is within these ranges.

A "polymerizable component" is any component which can be cured or solidified e.g. by heating to cause polymerization or chemical crosslinking, or e.g. by radiation-induced polymerization or crosslinking, or e.g. using a redox initiator or by any other radical forming process. A radically polymerizable component may contain only one, two, three or more radically polymerizable groups. Typical examples of radically polymerizable groups include unsaturated carbon groups, such as a vinyl group being present e.g. in a (meth)acrylate group.

A "monomer" is any chemical substance which can be characterized by a chemical formula, bearing radically polymerizable unsaturated groups (including (meth)acrylate groups) which can be polymerized to oligomers or polymers thereby increasing the molecular weight. The molecular weight of monomers can usually simply be calculated based on the chemical formula given.

"Polymer" or "polymeric material" are used interchangeably to refer to a homopolymer, copolymer, terpolymer etc. As used herein, "(meth)acryl" is a shorthand term referring to "acryl" and/or "methacryl". For example, a "(meth) acryloxy" group is a shorthand term referring to either an acryloxy group (i. e., $CH_2=CH-C(O)-O-$) and/or a methacryloxy group (i. e., $CH_2=C(CH_3)-C(O)-O-$).

An "ethylenically unsaturated acidic compound" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as COOH or CO—O—CO, phosphoric acid residues, such as —O—P(O)(OH)OH, phosphonic acid residues or sulfonic acid residues, such as $SO_3H$.

A "component having a resorcinol moiety" means a component comprising a benzene-1,3-dioyl structural unit.

A "solvent" means a liquid which is able to at least partially disperse or dissolve a component at ambient conditions (e.g. 23° C.). A solvent typically has a viscosity below 5 or below 1 or below 0.1 Pa*s.

As used herein, "hardening" or "curing" a composition are used interchangeably and refer to polymerization and/or crosslinking reactions including, for example, photopolymerization reactions and chemical polymerization techniques (e. g., ionic reactions or chemical reactions forming radicals effective to polymerize ethylenically unsaturated compounds) involving one or more materials included in the composition.

As used herein, a "dental surface" refers to tooth structures (e. g., enamel, dentin, and cementum) and bone.

A "dental restoration" refers to a material or means for restoring the function of missing tooth structure. Examples of dental restorations include dental filling materials, provisional crown and bridge materials, dental crowns and bridges, inlays, onlays, veneers, root canal fillers and dental posts.

A "self-etching composition" refers to a composition which bonds to a dental surface without pre-treating the dental surface with an etchant. Preferably, a self-etching composition can also function as a self-adhesive primer wherein no separate etchant or primer is used or be a self-adhesive composition.

A "self-adhesive composition" refers to a composition that is capable of bonding to a dental surface without pre-treating the dental surface with a primer or bonding agent. Preferably, a self-adhesive composition is also a self-etching composition wherein no separate etchant is used.

An "untreated dental surface" refers to a tooth or bone surface that has not been treated with an etchant, primer, or bonding agent prior to application of a self-etching adhesive or a self-adhesive composition. However, it may have been treated mechanically with a dental bur, grinding or polishing media, pumice etc.

An "unetched" dental surface refers to a tooth or bone surface that has not been treated with an etchant prior to application of a self-etching adhesive or a self-adhesive composition.

A "functionalised silane compound" is a silane compound bearing one or more moieties, which are able to undergo chemical reactions beyond condensation with OH-moieties of other silanes or on the surface of a filler. Examples of functionalised silane compounds include amino or (meth) acrylate functionalised silanes, like 3-aminopropyl trimethoxysilane or 3-(meth)acryloxypropyl trimethoxysilane.

A "non-surface treated filler" in the context of the invention is a filler having a surface which has not been exposed to reactive substances resulting in a modification of the surface of the filler to make the filler more compatible with other components of the composition.

"Ambient conditions" mean the conditions which the composition described in the present text is usually subjected to during storage and handling. Ambient conditions may, for example, be a pressure of 900 to 1100 mbar, a temperature of 10 to 40° C. and a relative humidity of 10 to 100%. In the laboratory ambient conditions are typically adjusted to 20 to 25° C. and 1000 to 1025 mbar.

A material or composition is "essentially or substantially free of" a certain component within the meaning of the invention, if the material or composition does not contain said component as an essential feature. Thus, said component is not willfully added to the composition or material either as such or in combination with other components or ingredient of other components. A composition or material being essentially free of a certain component usually contains the component in an amount of less than 1 wt. % or less than 0.1 wt. % or less than 0.01 wt. % with respect to the whole composition or material. Ideally the composition or material does not contain the said component at all. However, sometimes the presence of a small amount of the said component is not avoidable e.g. due to impurities.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and used in the specification and claims are to be understood as number as such and also as being modified by the term "about."

The term "about" can allow for a degree of variability in a value or range, e.g. within 10% or within 5% or within 1% of a given value or a given limit of a range.

The terms "comprise" or "contain" and variations thereof do not have a limiting meaning where these terms appear in the description and claims. The term "comprise" shall include also the terms "consist essentially of" and "consist of".

"And/or" means one or both. E.g., the expression component A and/or component B refers to a component A alone, component B alone, or to both component A and component B.

DETAILED DESCRIPTION

It has been found that the composition described in the text has a couple of advantageous properties. The dental composition described in the present text is sufficiently storage stable.

Compared to using x-ray opaque inorganic filler particles, the cross-linkable component comprising a brominated aromatic moiety does not settle during storage.

It was also found that the cross-linkable component comprising a brominated aromatic moiety are compatible with other components which are typically present in dental compositions, in particular dental adhesive compositions.

Further, the viscosity of a dental composition containing the cross-linkable component comprising a brominated aromatic moiety of the present text is not negatively affected. That is, a dental composition can be formulated which has a viscosity allowing the dental composition to be used as dental adhesive and restoration primer or dental sealant.

It was also surprisingly found that a dental composition containing the cross-linkable component comprising a brominated aromatic moiety described in the present text shows better adhesion to enamel and/or dentin surfaces than a dental composition containing cross-linkable component comprising an aromatic moiety, which is not brominated.

The dental composition described in the present text comprises a cross-linkable component comprising at least two polymerizable moieties like (meth)acrylate moieties and a brominated aromatic moiety as Component A, in particular a brominated resorcinol, catechol, tyrosol, benzoic acid, or phenol moiety. Component A does not contain an acidic moiety.

If desired, Component A can be characterized by the following properties alone or in combination:
  a) molecular weight: 400 to 800 g/mol or 450 to 750 g/mol;
  b) liquid at 23° C.;
  c) viscosity: 0.2 to 3 Pa*s at 23° C. and a shear rate of 100 1/s;
  d) having a refractive index in the range of 1.52 to 1.56 or 1.53 to 1.55.

A combination of the following properties can sometimes be preferred: a) and b); a) and c); b) and c); a), c) and d). If desired, the properties can be determined as outlined in the example section.

According to one embodiment, the brominated polymerizable monomer(s) comprises a brominated resorcinol moiety according to the following formula

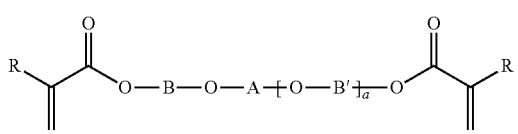

with:

B—O-A-[—O—B'—]$_a$ representing the monomer backbone as linkage between the reactive (meth)acrylate moieties, a=0 or 1, A being

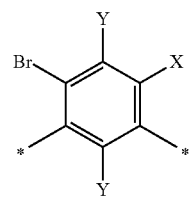

A being always attached as aryl-alkyl ether onto B and/or B',

B being selected from:

\*—(CH$_2$)$_b$—\*, \*—(CH$_2$—CH$_2$—O—CH$_2$—CH$_2$)—\*,
\*—(CH$_2$—CH$_2$—O—CH$_2$—CH$_2$—CH$_2$)—\*,
\*—(CH$_2$—CH$_2$—CH$_2$—O—CH$_2$—CH$_2$—CH$_2$)-\*,

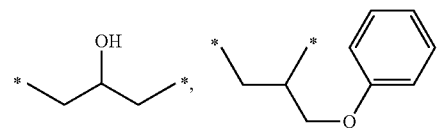

B being always attached as alkyl ester onto the (meth)acrylate reactive moiety, b=2 to 6, B' being selected from \*—(CH$_2$)$_{b'}$—\*, \*—(CH$_2$—CH$_2$—O—CH$_2$—CH$_2$)—\*,

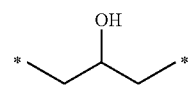

B' being always attached as alkyl ester onto the (meth)acrylate reactive moiety, b'=2 to 6, R=H, methyl, X being selected from H, methyl, ethyl, hexyl, tert-butyl, Br, Y=H, Br, "\*" representing those site(s) of a moiety of the monomer, where that moiety is bonded to another moiety of the monomer.

Particular examples thereof include the following monomers or mixtures thereof:

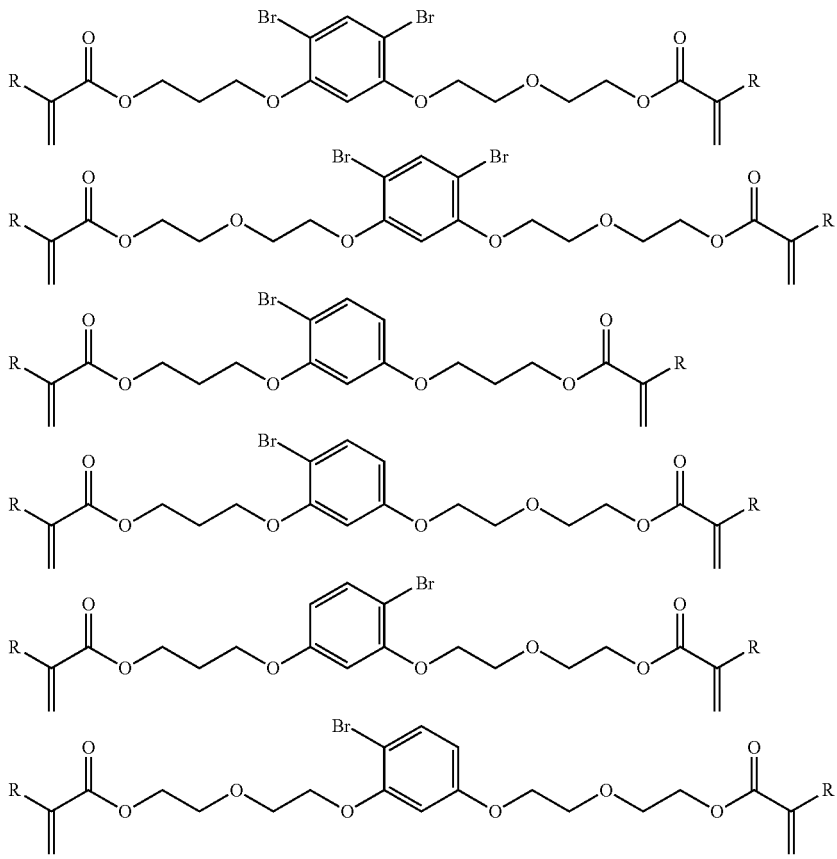

R being independently selected from H and CH$_3$.

According to one embodiment, the brominated polymerizable monomer(s) comprises a brominated catechol moiety according to the following formula

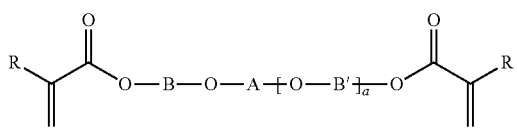

with:

B—O-A-[—O—B'—]$_a$ representing the monomer backbone as linkage between the reactive (meth)acrylate moieties, a=0 or 1, A being selected from:

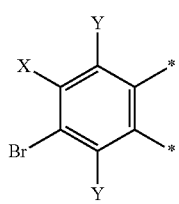

A being always attached as aryl-alkyl ether onto B and/or B',

B being selected from:
*—(CH$_2$)$_b$—*,  *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)-*,

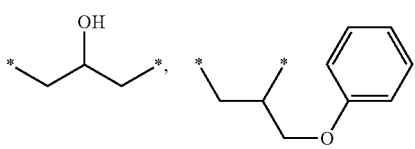

B being always attached as alkyl ester onto the (meth) acrylate reactive moiety, b=2 to 6, B' being selected from *—(CH$_2$)$_{b'}$—*, *—(CH$_2$—CH$_2$—O—CH$_2$—CH$_2$)—*,

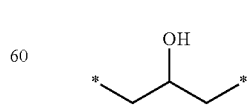

B' being always attached as alkyl ester onto the (meth) acrylate reactive moiety, b'=2 to 6, R=H, methyl, X being selected from H, methyl, ethyl, hexyl, tert-butyl, Br,
Y=H, Br,
"*" representing those site(s) of a moiety of the monomer, where that moiety is bonded to another moiety of the monomer.
Particular examples thereof include the following monomers or mixtures thereof:
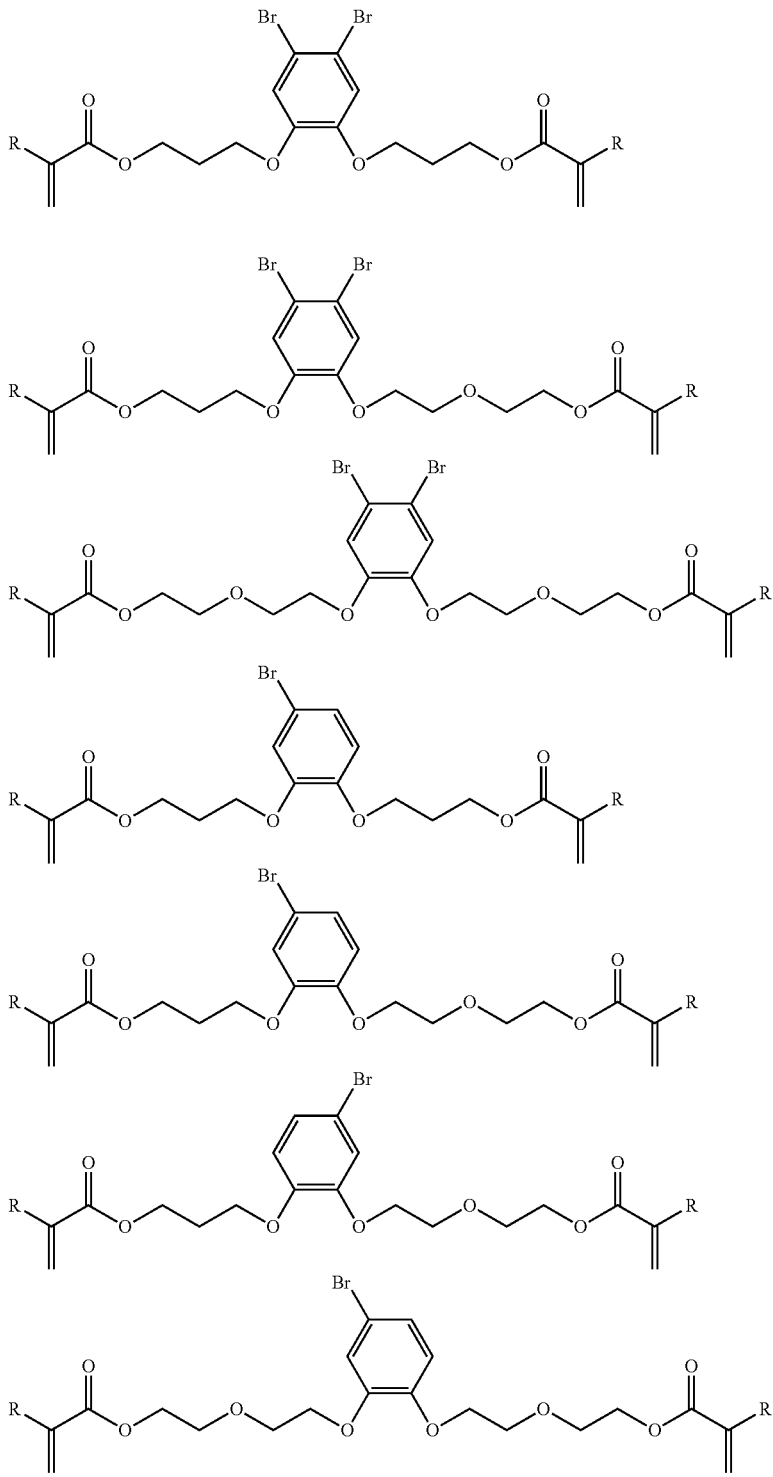
R being independently selected from H and $CH_3$.

According to one embodiment, the brominated polymerizable monomer(s) comprises a brominated tyrosol moiety according to the following formula:

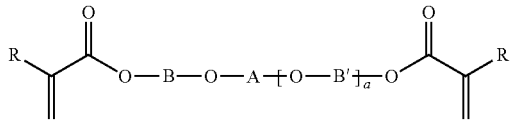

with:
B—O-A-[—O—B'—]$_a$ representing the monomer backbone as linkage between the reactive (meth)acrylate moieties,
a=0 or 1,
A being

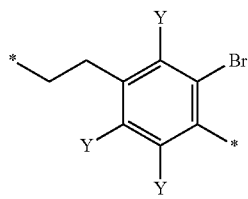

A being always attached as aryl-alkyl ether onto B and/or B',
B being selected from:
*—(CH$_2$)$_b$—*, *—(CH$_2$—CH$_2$—O—CH$_2$—CH$_2$)—*,
*—(CH$_2$—CH$_2$—O—CH$_2$—CH$_2$—CH$_2$)—*,
*—(CH$_2$—CH$_2$—CH$_2$—O—CH$_2$—CH$_2$—CH$_2$)-*,

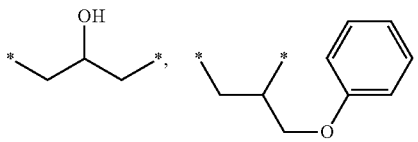

B being always attached as alkyl ester onto the (meth)acrylate reactive moiety,
b=2 to 6,
B' being selected from *—(CH$_2$)$_{b'}$—*, *—(CH$_2$—CH$_2$—O—CH$_2$—CH$_2$)-*,

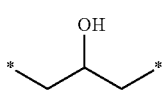

B' being always attached as alkyl ester onto the (meth)acrylate reactive moiety,
b'=2 to 6,
R=H, methyl,
X being selected from H, methyl, ethyl, hexyl, tert-butyl, Br,
Y=H, Br,
"*" representing those site(s) of a moiety of the monomer, where that moiety is bonded to another moiety of the monomer.

According to one embodiment the polymerizable monomer(s) are selected from:

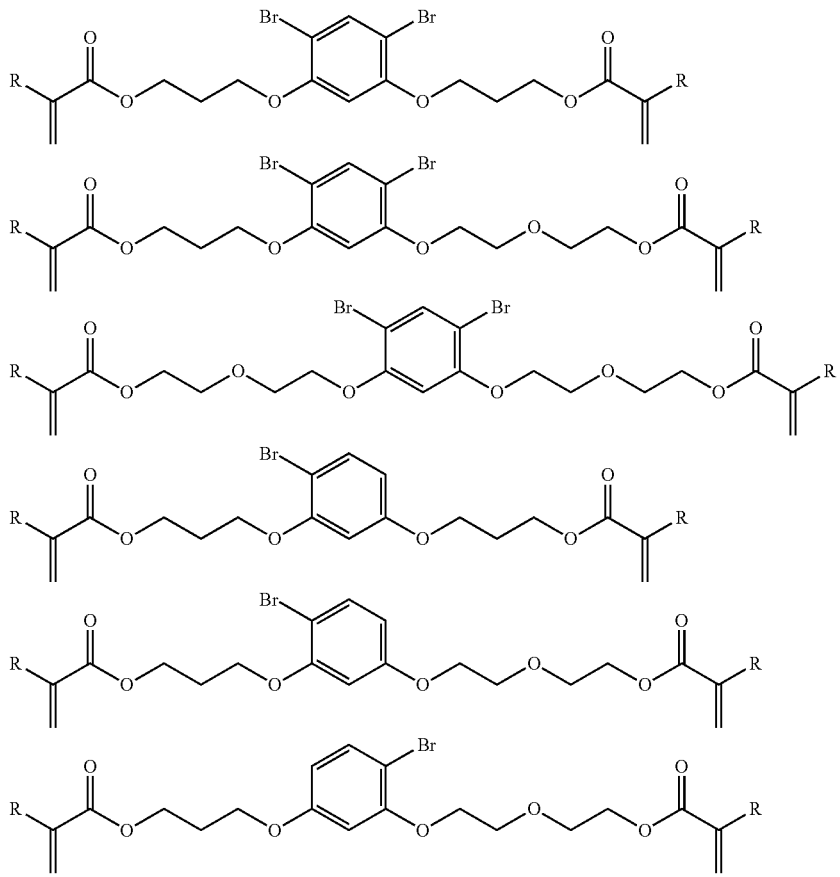

-continued
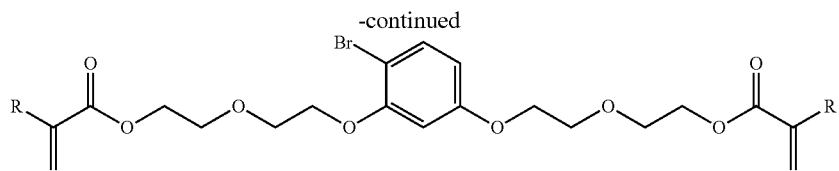
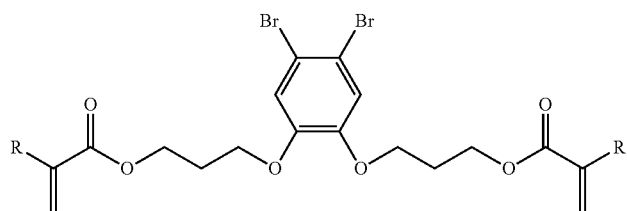
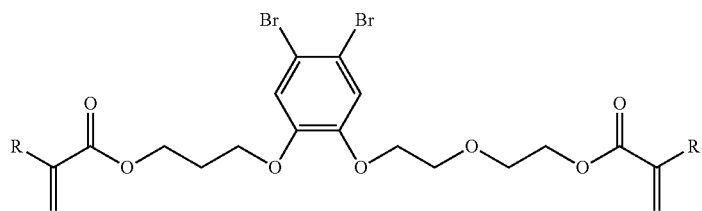
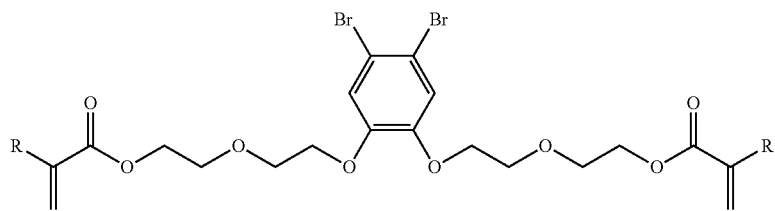
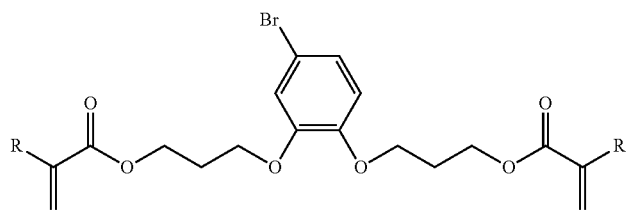
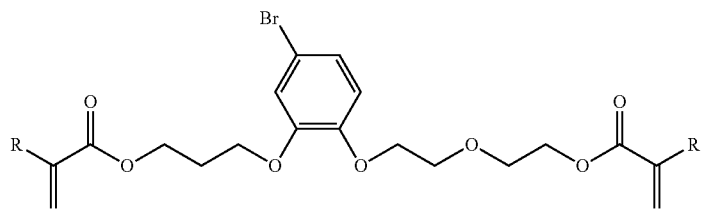
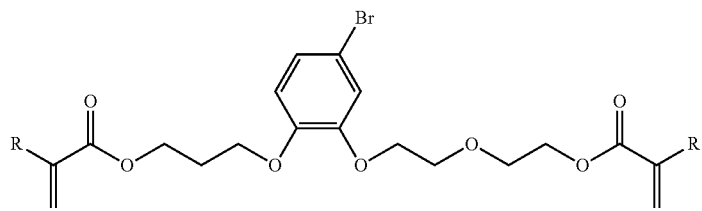
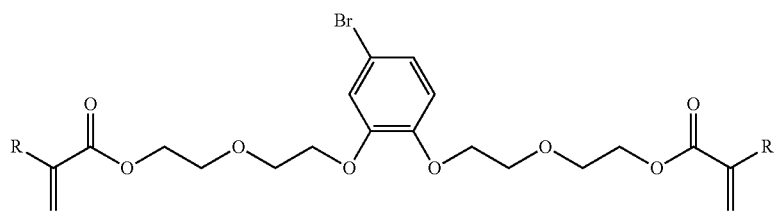

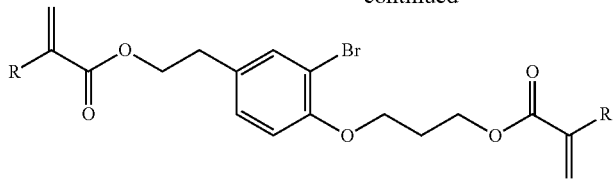

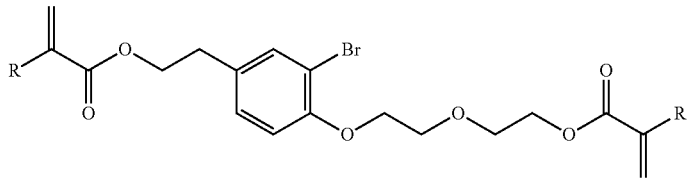

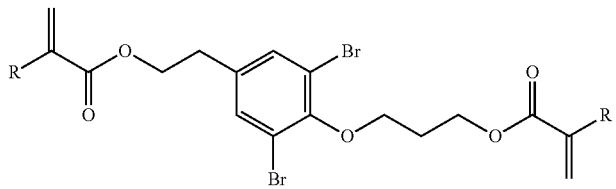

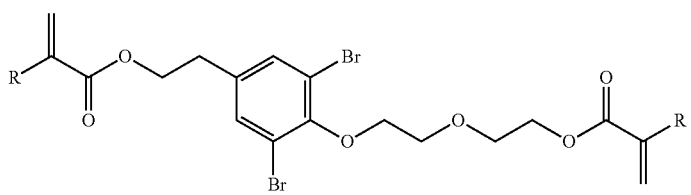

R being independently selected from H and CH$_3$, and mixtures thereof.

A mixture of different components which was found to be particularly useful contains symmetrically substituted molecules as well as non-symmetrically substituted molecule.

The polymerizable monomers according to the above formula (I) can be synthesized e.g. as described in the example section below.

When doing so, the skilled person will realize that depending on the polymerizable monomer (I) during synthesis a single non-symmetrical compound is obtained as well as a mixture containing different non-symmetrical components or a mixture containing minor symmetrical components besides the major non-symmetrical compound is obtained.

For a polymerizable monomer according to formula (I) containing a non-symmetrical backbone based on a non-symmetrically substituted aromatic moiety, the synthesis will result either in a single non-symmetrical compound or in a composition containing 100 mol-% of non-symmetrical components.

Unless further purified, the synthesis of a polymerizable monomer according to formula (I) containing a non-symmetrical backbone which is based on a symmetrically substituted aromatic moiety, will usually result—due to statistics—in a composition containing about 50 mol-% of the non-symmetrical compound as the major component besides about 25 mol-% each of symmetrical compounds as minor components.

Thus, mixtures of two, three or more of the polymerizable monomers according to formula (I) can be used, and are sometimes desired.

Using a mixture of the following components is sometimes preferred:

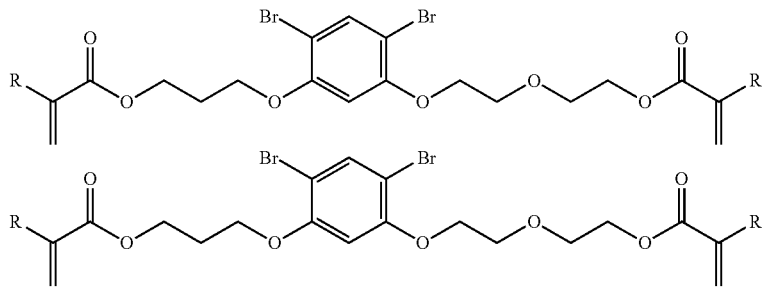

-continued

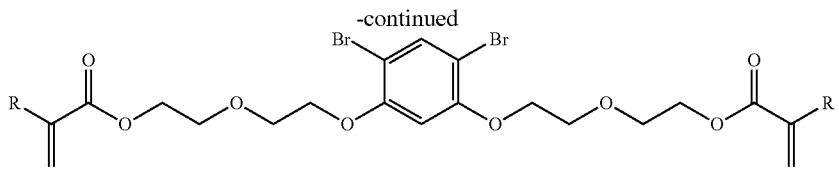

R being always independently selected from H and CH$_3$.
In the Example section this mixture is referred to as DIBROERMA.

Component A is typically present in the following amounts:
  Lower amount: at least 1 or at least 5 or at least 10 wt. %;
  Upper amount: at most 60 or at most 50 or at most 40 wt. %;
  Range: from 1 to 60 or from 5 to 50 wt. % or 10 to 40 wt. %;
wt. % with respect to the weight of the whole composition.

The composition described in the present text comprises one or more non-brominated ethylenically unsaturated component(s) with acidic moiety as Component B.

The nature and structure of Component B is not particularly limited unless the desired result cannot be achieved.

Examples of the acidic moiety include carboxylic acid residues, phosphoric acid residues, phosphonic acid residues or sulfonic acid residues.

In one embodiment, the polymerizable component having an acidic moiety can be represented by the following formula $A_nBC_m$ B being a backbone group, such as (i) linear or branched C$_1$ to C$_{12}$ alkyl, optionally substituted with OH, (ii) C$_6$ to C$_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, A being an ethylenically unsaturated group attached to the backbone group, such as a (meth)acryloyl moiety, C being an acidic group attached to the backbone group, with m, n=1, 2, 3, 4, 5 or 6, wherein the acidic group comprises one or more carboxylic acid or anhydride residues, such as —COOH or —CO—O—CO—, phosphoric acid residues, such as —O—P(O)(OH)OH, phosphonic acid residues or sulphonic acid residues, such as —SO$_3$H.

Specific examples of ethylenically unsaturated acidic compounds include, but are not limited to glycerol phosphate mono(meth)acrylates, glycerol phosphate di(meth)acrylates, hydroxyethyl (meth)acrylate phosphates, bis glycerol phosphate di(meth)acrylates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, di or tri(meth)acrylated citric acid, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like.

The reaction products of (meth)acrylic acid with alkane diols (e.g. C$_2$ to C$_{20}$ or C$_2$ to C$_{12}$ or C$_6$ to C$_{10}$) and phosphorous oxide were found to be suitable as well.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bisphosphonic acids as disclosed for example in US 2004/0206932 A1 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Fuchigami et al.) and EP 1 051 961 A1 (Hino et al.).

Typical compositions also include an ethylenically unsaturated acidic compound with at least one phosphoric acid group (e.g. P—OH moiety).

Examples of preferred phosphoric acid group-containing polymerizable monomer include 6-(meth)acryloxyhexyl dihydrogenphosphate, 7-(meth)acryloxyheptyl dihydrogenphosphate, 8-(meth)acryloxyoctyl dihydrogenphosphate, 9-(meth)acryloxynonyl dihydrogenphosphate, 10-(meth)acryloxydecyl dihydrogenphosphate, 11-(meth)acryloxyundecyl dihydrogenphosphate, 12-(meth)acryloxydodecyl dihydrogenphosphate, 16-(meth)acryloxyhexadecyl dihydrogenphosphate, 20-(meth)acryloxyeicosyl dihydrogenphosphate, bis[6-(meth)acryloxyhexyl]hydrogenphosphate, bis[8-(meth)acryloxyoctyl]hydrogenphosphate, bis[9-(meth)-acryloxynonyl]hydrogenphosphate, bis[10-(meth)acryloxydecyl]hydrogenphosphate, 1,3-di(meth)acryloxypropyl dihydrogenphosphate, 2-(meth)acryloxyethylphenyl hydrogen-phosphate, 2-(m eth)acryloxyethyl-2-b romoethyl hydrogenphosphate, (5-methacryloxy)pentyl-3-phosphonopropionate, (6-methacryl oxy)hexyl-3-hosphonopropionate, (10-methacryloxy)decyl-3-phosphonopropionate, (6-methacryloxy)hexyl-3-phosphonoacetate, (10-methacryloxy)decyl-3-phosphonoacetate, 2-methacryloxyethyl (4-methoxyphenyl) hydrogenphosphate and 2-methacryloxypropyl (4-methoxyphenyl) hydrogenphosphate and mixtures thereof.

Mixtures of different Components B can be used, if desired.

Component B is typically present in the following amount(s):
Lower limit: at least 1 or at least 2 or at least 3 wt. %;
Upper limit: utmost 30 or utmost 25 or utmost 20 wt. %;
Range: from 1 to 30 or from 2 to 25 or from 3 to 20 wt. %; wt. % with respect to the whole amount of the composition.

The composition described in the present text comprises one or more photoinitiator(s) as Component C.

The nature and structure of the photoinitiator is not particularly limited unless the intended purpose is not negatively affected.

Suitable photoinitiator(s) for free radical polymerization are generally known to the person skilled in the art dealing with dental materials.

As photoinitiator(s), those which can polymerize the polymerizable monomer(s) by the action of visible light having a wavelength of 350 nm to 500 nm are preferred.

Suitable photoinitiator(s) often contain an alpha di-keto moiety, an anthraquinone moiety, a thioxanthone moiety or benzoin moiety.

Examples of photoinitiator(s) include camphorquinone, 1-phenyl propane-1,2-dione, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone.

Component C is typically present in the following amount(s):
Lower limit: at least 0.1 or at least 0.2 or at least 0.5 wt. %;
Upper limit: utmost 4 or utmost 3 or utmost 2 wt. %;
Range: from 0.1 to 4 or from 0.2 to 3 or from 0.5 to 2 wt. %;
wt. % with respect to the whole amount of the composition.

The composition described in the present text comprises one or more reducing agents as Component D.

As reducing agent amines, in particular secondary and tertiary amines can be used. Suitable examples include triethanolamine, diethanolamine, methyl diethanolamine, 2-dimethylaminoethyl (meth)acrylate, 3-dimethylaminopropyl (meth)acrylate, 4-dimethylaminobutyl (meth)acrylate, 6-dimethylaminohexyl (meth)acrylate, 10-dimethylaminodecyl (meth)acrylate, 4-dimethylaminophenetyl alcohol, 4-diethylaminophenetyl alcohol, 4-dipropylaminophenetyl alcohol, N,N-di(2-hydroxyethyl)-p-toluidine, N,N-di(2-hydroxypropyl)-p-toluidine, N,N-dimethyl-p-toluidine, N,N-dipropyl-p-toluidine, N,N-diethyl-p-toluidine, N,N-diethoxyethyl-p-toluidine, N,N-dibutoxy ethyl-p-toluidine, N,N-di(polyoxyethylene)oxyethyl-p-toluidine, hexamethylenediamine, a dimethylamine aqueous solution, pentamethylenediamine, diethylamine, ethylenediamine, 2-aminoethanol, triethylamine and 2-dimethylaminoethanol.

In particular the following amines were found to be useful: N,N-dimethyl-aminoethyl methacrylate, ethyl 4-dimethylaminobenzoate, methyl 4-dimethylaminobenzoate, triethanolamine, N,N-dimethyl-p-toluidine, N,N-di-2-hydroxyethyl-p-toluidine, and isoamyl 4-dimethylaminobenzoate.

Moreover, ternary photopolymerization initiating systems comprising a photoinitiator an electron donor and an onium salt as described in U.S. Pat. No. 6,187,833 (Oxman et al.), U.S. Pat. No. 6,025,406 (Oxman et al), U.S. Pat. No. 6,043,295 (Oxman et al.), U.S. Pat. No. 5,998,495 (Oxman et al.), U.S. Pat. No. 6,084,004 (Weinman et al.) and U.S. Pat. No. 6,765,036 (Dede et al.) can be used, too.

Other reducing agents, like sodium sulfinate derivatives and organometallic compounds can be used, as well. These compounds may be used singly or in admixture.

Specific examples of sulfinic acid components include benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid.

Particularly suitable sulfinic acid component are sodium toluenesulfinate or sodium benzenesulfinate and their hydrates.

It is also possible to use a quaternary photopolymerization initiating system comprising two different photoinitiators and two different reducing agents.

Component D is typically present in the following amount(s):
Lower limit: at least 0.1 or at least 0.3 or at least 0.5 wt. %;
Upper limit: utmost 4 or utmost 3 or utmost 2 wt. %;
Range: 0.1 to 4 or 0.3 to 3 or 0.5 to 2 wt. %;
wt. % with respect to the whole amount of the composition.

The composition described in the present text may also comprise one or more filler(s) as Component E.

Fillers may be selected from one or more of a wide variety of materials suitable for incorporation in compositions used for dental applications, such as fillers currently used in dental restorative compositions, and the like.

The filler(s) which may be used in the compositions of the present text is preferably finely divided. The filler(s) can have a unimodal or polymodal (e.g., bimodal) particle size distribution. Typically, the maximum particle size (the largest dimension of a particle, generally, the diameter) of the filler(s) is less than 20 µm, more typically less than 10 µm, and most preferably less than 5 µm. Typically, the average primary particle size of the filler(s) is less than 0.1 µm, and more typically less than 0.075 µm.

The compositions may include a filler comprising an inorganic material. It can also be a crosslinked organic material that is insoluble in the resin system, and is optionally filled with inorganic filler. The filler(s) should in be nontoxic and suitable for use in the mouth or a patient. The filler(s) can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Evonik Industries AG, Essen, Germany, and CAB-O-SIL M5 silica from Cabot Corp., Tuscola, Ill.).

Examples of suitable organic filler particles include filled or unfilled pulverized polycarbonates, polyepoxides, and the like.

Suitable non-acid-reactive filler particles include quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially useful in certain embodiments.

Other suitable fillers are disclosed in U.S. Pat. No. 6,387,981 (Zhang et al.); U.S. Pat. No. 6,572,693 (Wu et al.); U.S. Pat. No. 6,730,156 (Windisch); and U.S. Pat. No. 6,899,948 (Zhang); as well as in International Publication No. WO 03/063804 (Wu et al.). Filler components described in these references include nanosized silica particles, nano-sized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.). Fumed or precipitated silica has been found to be particularly useful.

Examples of non-surface treated fillers which can be used include AEROSIL™, including "OX 50," "90", "130", "150", "200", "300", and "380" silicas (Evonik Industries AG, Essen, Germany), and Cab-O-Sil, including "LM-150", "M-5", "H-5", "EH-5" silicas (Cabot Corp., Tuscola, Ill.), and HDK™, including "S13", "V15", "N20", "T30", "T40" silicas (Wacker-Chemie AG, Munich, Germany), and Orisil™, including "200", "300", "380" silicas (Orisil, Lviv, Ukraine).

Further examples of silica fillers according to component (G) include, but are not limited to precipitated silicas such as those available under the brands Sipernat™ Ultrasil™, and Acematt™ (Evonik Industries AG, Essen, Germany), Lo-Vel™ and Hi-Sil™ (PPG Industries, Pittsburgh, Pa.), Zeosil™ (Rhodia, Paris la Defense, France). Suitable pyrogenic silica fillers can have a specific surface area of 100 to 400 m²/g.

The surface of the filler particles can be pre-treated with a coupling agent in order to enhance the bond between the filler and the resin.

A suitable silane composition may comprise (meth)acrylate functional silane(s) and amino functional silane(s).

The nature and structure of the (meth)acrylate functional silanes is not particularly limited unless the intended purpose is not negatively affected.

Suitable functionalized silane components include alkoxy silane(s), preferably a trialkoxy silane comprising a (meth)acrylate group and at least one group that can hydrolyse with water.

Typical embodiments can be characterized by the following formula:

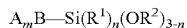

$$A_mB\text{—}Si(R^1)_n(OR^2)_{3-n}$$

with A comprising a (meth)acryl moiety,

B comprising a spacer group, such as (i) linear or branched $C_1$ to $C_{12}$ alkyl, (ii) $C_6$ to $C_{12}$ aryl, (iii) organic group having 2 to 20 carbon atoms bonded to one another by one or more ether, thioether, ester, thioester, thiocarbonyl, amide, urethane, carbonyl and/or sulfonyl linkages, $R^1$ comprising an alkyl group (e.g. $C_1$ to $C_6$) or an aryl group (e.g. $C_6$ to Cu), and $R^2$ comprising an alkyl group (e.g. $C_1$ to $C_6$), with m=1, 2, 3 or 4 and n=0, 1 or 2.

Examples of (meth)acrylate functionalized trialkoxy silanes include, but are not limited to 3-(meth)acryloxypropyl trimethoxysilane, 3-(meth)acryloxypropyl triethoxysilane, 3-(meth)acryloxypropyl tris(methoxyethoxy)silane, 3-(meth)acryloxy-propenyl trimethoxysilane, (meth)acryloxyethyldimethyl (3-trimethoxysilylpropyl)-ammonium chloride, N-(3-(meth)acryl oxy-2-hydroxypropyl)-3-aminopropyltriethoxy-silane, O-((meth)acryloxyethyl)-N-(triethoxysilylpropyl)urethane, (meth)acryloxymethyl trimethoxysilane, (meth)acryloxymethyl triethoxysilane, (meth)acryloxymethyl methyldimethoxysilane, (meth)acryloxymethyl methyldiethoxysilane, (meth)acryloxyoctyl trimethoxysilane, [(meth)acryloxymethyl]phenethyl trimethoxysilane, O-[(meth)acryloxy-ethyl]-N-(triethoxysilylpropyl)carbamate, (meth)acryloxypropyl triisopropoxysilane, (meth)acryloxypropyl methyldimethoxysilane, (meth)acryloxypropyl methyldiethoxy-silane, 3-(meth)acryloxypropyl dimethylmethoxysilane, 3-(meth)acryloxypropyl dimethylethoxysilane, (meth)acryloxymethyl dimethylmethoxysilane, (meth)acryloxymethyl dimethylethoxysilane, oligomeric hydrolysate of 3-(meth)acryloxypropyl trimethoxysilane, oligomeric hydrolysate of 3-(meth)acryl oxypropyl triethoxysilane. These organosilane compounds may be used alone or admixtures thereof.

The surface-treatment of the filler components can be done before the filler particles are combined with the other components of the dental composition.

Alternatively, or in addition, the organosilane compounds can be added to the dental composition as a separate component or mixture of components. In this case, typically an in-situ silanization takes place. Such a reaction is e.g. described in U.S. Pat. No. 7,968,617 B2 (Thalacker et al.). This reference is herewith incorporated by reference. The molecular weight of this component is typically within a range from 200 to 400 g/mol. Non-surface treated fillers can be used as well and are sometimes preferred.

If present, Component E is typically present in the following amount(s):
Lower limit: at least 1 or at least 3 or at least 5 wt. %;
Upper limit: utmost 25 or utmost 20 or utmost 15 wt. %;
Range: 1 to 25 or 3 to 20 or 5 to 15 wt. %;
wt. % with respect to the whole amount of the composition.

The dental composition described in the present text may comprise one or more solvent(s) other than water as Component F.

Adding solvent(s) or co-solvent(s) may help to adjust the viscosity and consistency of the composition.

Examples of solvents according to Component F include, but are not limited to linear, branched or cyclic, saturated or unsaturated alcohols, ketones, esters, ethers or mixtures of two or more of said type of solvents with 2 to 10 C atoms. Preferred alcoholic solvents include methanol, ethanol, isopropanol and n-propanol.

Other suitable organic solvents are THF, acetone, methylethyl ketone, cyclohexanol, toluene, alkanes and acetic acid alkyl esters, in particular acetic acid ethyl ester.

It is possible to use the above-mentioned solvents alone or as a mixture of two or more of any of these solvents, if the solvent mixtures do not impair the adhesive properties to such an extent that the desired result cannot be obtained.

If present, Component F is present in the following amount(s):
Lower limit: at least 2 or at least 5 or at least 10 wt. %;
Upper limit: utmost 50 or utmost 30 or utmost 20 wt. %;
Range: 2 to 50 or 5 to 30 or 10 to 20 wt. %;
wt. % with respect to the whole amount of the composition.

The composition described in the present text may comprise water as Component G. If present, water is typically provided in the form of de-ionized water.

Water may be present in the following amount(s):
Lower limit: at least 1 or at least 3 or at least 10 wt. %;
Upper limit: utmost 30 or utmost 25 or utmost 20 wt. %;
Range: 1 to 30 or 3 to 25 or 5 to 20 wt. %;
wt. % with respect to the whole amount of the composition.

Besides the cross-linkable component(s) comprising a brominated aromatic moiety according to Component A, the composition described in the present text may also comprise other cross-linkable, non-acidic component(s) being different from Component A as Component H.

Component H is typically a non-brominated, ethylenically unsaturated compound without acidic moiety(s).

Suitable polymerizable component(s) without acidic moiety(s) can be characterized by the following formula:

$A_n B A_m$ with A being an ethylenically unsaturated group attached to backbone B, such as a (meth)acryl moiety, B being selected from (i) linear or branched $C_1$ to $C_{12}$ alkyl, (ii) $C_6$ to $C_{12}$ aryl, optionally substituted with other functional groups (e.g. OH), or (iii) organic group having 4 to 20 carbon atoms bonded to one another by one or more ether, ester, amide, urethane, carbonyl and/or sulfonyl linkages, m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Rohm Plex™ 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274 (Boettcher et al.)), and acrylated oligomers (see e.g. U.S. Pat. No. 4,642,126 (Zador et al.)); and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used if desired.

Further polymerizable components which may be present include di(meth)acrylates of ethoxylated bis-phenol A, for example 2,2'-bis(4-(meth)acryl-oxytetraethoxyphenyl)propanes, 2,2'-bis(4-(meth)acryloxytriethoxyphenyl)propanes, 2,2'-bis(4-(meth)acryloxydiethoxyphenyl)propanes, urethane (meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in U.S. Pat. No. 4,795,823 (Schmitt et al.), such as bis[3[4]-methacryl-oxymethyl-8(9)-tricyclo[$5.2.1.0^{2.6}$]decylm-ethyl triglycolate. Suitable are 2,2-bis-4(3-methacryloxypropoxy)phenylpropane, urethane (meth)acrylates and di(meth)acrylates of bishydroxymethyltricyclo-($5.2.1.0^{2.6}$) decane.

Further examples for polymerizable component(s) without an acidic moiety are the dimethycrylate and the diacrylate derived from tricyclodecane-dimethanol (mixture of isomers), reaction products of tricyclodecane-dimethanol with isocyanatoethyl (meth)acrylate, reaction products of tricyclodecane-diisocyanate with hydroxyethyl (meth)acrylate or hydroxypropyl (meth)acrylate.

These ethylenically unsaturated monomers can be employed in the dental composition(s) either alone or in combination with the other ethylenically unsaturated monomers.

In addition or besides those components, other hardenable components which can be added include oligomeric or polymeric compounds, such as polyester (meth)acrylates, polyether (meth)acrylates, polycarbonate (meth)acrylates and polyurethane (meth)acrylates. The molecular weight of these compounds is typically less than 20,000 g/mol, particularly less than 15,000 g/mol and in particular less than 10,000 g/mol.

Polymerizable monomers comprising a hydroxyl moiety and/or a 1,3-diketo moiety can also be added. Suitable compounds include 2-hydroxyethyl methacrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di(meth)acrylate, 3-hydroxypropyl-1,2-di(meth)acrylate, N-(meth)acryloyl-1,2-dihydroxypropylamine, N-(m eth)-acryloyl-1,3-dihydroxypropyl amine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like. 2-Hydroxyethyl (meth)acrylate, 2-hydroxypropyl (meth)acrylate and 2,3-dihydroxypropyl (meth)acrylate are sometimes preferred.

If present, Component H is typically present in the following amount(s):
Lower limit: at least 10 or at least 20 or at least 30 wt. %;
Upper limit: utmost 80 or utmost 70 or utmost 60 wt. %;
Range: 10 to 80 or 20 to 70 or 30 to 60 wt. %;
wt. % with respect to the whole amount of the composition.

The composition described in the present text may also comprise one or more additive(s) as Component I.

Additives of adjuvants which can be used include inhibitors or retarders, stabilizers, dyes, fluoride release agents, surface tension depressants and wetting aids, antioxidants, and other ingredients well known to those skilled in the art. The amounts and types of each ingredient in the composition should be adjusted to provide the desired physical and handling properties before and after polymerization.

Examples of stabilizers include 2,6-di-tert-butyl-4-methylphenol (butylated hydroxytoluene, BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, and 2-(2'-hydroxy-5'-methacryloxyethylphenyl)-2H-benzotriazole.

Examples of photobleachable colorants include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725 (Tom et al.). The colour of the compositions of the invention may be additionally imparted by a sensitizing compound.

Examples of fluoride release agents are naturally occurring or synthetic fluoride minerals such as sodium fluoride, fluoride glass such as fluoroaluminosilicate glass, simple and complex inorganic fluoride salts such as potassium zinc fluoride and potassium hexa fluorotitanate, simple and complex organic fluoride salts such as tetraethylammonium tetrafluoroborate or combinations thereof. These fluoride sources can optionally be treated with surface treatment agents.

If present, Component I is present in the following amount(s):
Lower limit: at least 0.01 or at least 0.1 or at least 0.2 wt. %;
Upper limit: utmost 5 or utmost 3 or utmost 2 wt. %;
Range: 0.01 to 5 or 0.1 to 3 or 0.2 to 2 wt. %;
wt. % with respect to the whole amount of the composition.

In certain embodiments the composition described in the present text can be characterized by the following properties alone or in combination:
a) viscosity: 0.01 to 3 Pa*s or 0.02 to 2 Pa*s at 23° C. and a shear rate of 100 s$^{-1}$;
b) pH-value: 0.8 to 4, if determined with wet pH-sensitive paper;
c) shear bond strength to enamel: at least 12 MPa or at least 20 MPa or at least 25 MPa according to ISO 29022 (2013-09);
d) shear bond strength to dentin: at least 12 MPa or at least 20 MPa or at least 25 MPa according to ISO 29022 (2013-09);
e) being x-ray visible;
f) being radiation curable;
g) being storage stable.

If desired, the respective properties can be determined as described in the example section.

A combination of the following properties is sometimes preferred: a) and b); a), b) and c); a), b), c) and d); a), b), c), and e); a), b), c), e) and f); a), b), e), f) and g).

That is, the composition described in the present text has a viscosity, which allows an easy application of the composition on the surface of a dental structure through a nozzle, e.g. using a syringe, brush or dropper bottle. Further, the composition is acidic, i.e. it is able to etch the surface of a dental structure.

The composition is also x-ray visible, i.e. the composition can be detected with an x-ray device and imaging system.

The composition is also storage stable, i.e. it remains a homogenous mixture during storage and use.

Due to the presence of radiation-curable component(s) and an initiator system, the composition is radiation-curable, i.e. it can be cured by applying visible or UV light.

According to one embodiment, the composition contains the components in the following amounts:
Component A (brominated monomer): 10 to 50 wt. %,
Component B (acidic monomers): 2 to 20 wt. %,
Component C (photoinitiator): 0.1 to 3 wt. %,
Component D (reducing agent): 0.1 to 3 wt. %,
Component E (filler): 0 to 25 wt. %,
Component F (solvent): 0 to 40 wt. %,
Component G (water): 0 to 20 wt. %,
Component H (non-acidic monomers): 0 to 40 wt. %,
Component I (additive): 0 to 10 wt. %,
wt. % with respect to the weight of the whole composition.

According to another embodiment, the composition contains the components in the following amounts:
Component A (brominated monomer): 10 to 50 wt. %,
Component B (acidic monomers): 5 to 20 wt. %,
Component C (photoinitiator): 0.1 to 3 wt. %,
Component D (reducing agent): 0.1 to 3 wt. %,
Component E (filler): 1 to 25 wt. %,
Component F (solvent): 1 to 40 wt. %,
Component G (water): 1 to 20 wt. %,
Component H (non-acidic monomers): 1 to 40 wt. %,
Component I (additive): 1 to 10 wt. %,
wt. % with respect to the weight of the whole composition.

According to a further embodiment, the composition contains the components in the following amounts:
Component A (brominated monomer): 20 to 50 wt. %,
Component B (acidic monomers): 5 to 20 wt. %,
Component C (photoinitiator): 0.1 to 3 wt. %,
Component D (reducing agent): 0.1 to 3 wt. %,
Component E (filler): 1 to 25 wt. %,
Component F (solvent): 1 to 30 wt. %,
Component G (water): 1 to 20 wt. %,
Component H (non-acidic monomers): 10 to 40 wt. %,
Component I (additive): 1 to 10 wt. %,
wt. % with respect to the weight of the whole composition.

According to another embodiment, the composition described in the present text is characterized as follows:
Component A:
being selected from:

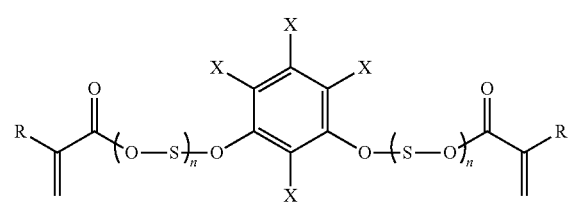

wherein
R is individually selected from H and $CH_3$;
S is individually selected from a linear or branched $C_2$-6 spacer group; and
X is individually selected from H and Br, with the proviso that at least one Br is present and mixtures thereof and being present in an amount of 20 to 50 wt. %,
Component B:
being selected from:

$A_nBC_m$ with B being a backbone group selected from (i) linear or branched $C_1$ to $C_{12}$ alkyl, optionally substituted with OH, (ii) $C_6$ to $C_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH,
A being an ethylenically unsaturated group attached to the backbone group, C being an acidic group attached to the backbone group, with m, n=1, 2, 3, 4, 5 or 6,
wherein the acidic group comprises one or more phosphoric acid residues and mixtures thereof and
being present in an amount of 5 to 20 wt. %,
Component C:
being selected from components comprising an alpha di-keto moiety, an anthraquinone moiety, a thioxanthone moiety or benzoin moiety and mixtures thereof and
being present in an amount of 0.1 to 3 wt. %,
Component D:
being selected from secondary and tertiary amines and mixtures thereof and
being present in an amount of 0.1 to 3 wt. %,
Component E:
being selected from submicron silica particles thereof and
being present in an amount of 1 to 20 wt. %,
Component F:
being selected from alcohols, ketones, esters, ethers and mixtures thereof and
being present in an amount of 1 to 30 wt. %,
Component G:
being present in an amount of 1 to 20 wt. %,
Component H:
being selected from non-brominated, ethylenically unsaturated component(s) without acidic moiety(s) and mixtures thereof and
being present in an amount of 10 to 40 wt. %,
Component I:
being selected from inhibitors, retarders, stabilizers, dyes, fluoride release agents, wetting agents, antioxidants and mixtures thereof and
being present in an amount of 1 to 10 wt. %,
wt. % with respect to the weight of the whole composition.

According to one embodiment, the composition described in the present text does typically not contain the following component(s) alone or in combination:
halogenated solvent(s) in an amount above 2 wt. %, or above 1 wt. %;
aldehydes in an amount above 1 wt. %;
solvent(s) with a boiling point above 150° C. in an amount above 2 wt. %, or above 1 wt. %;
bisphenol A-glycidyl methacrylate in an amount of more than 5 or 10 wt. %;
coloured dyes or pigments which are not photo-bleachable in an amount above 1 wt. %, or above 0.5 wt. %;
filler(s) with an average particle size larger than 50 µm in an amount above 1 wt. %, or above 0.5 wt. %;
wt. % with respect to the weight of the whole composition.

The composition described in the present text can be produced as follows:
providing the components of the composition,
mixing the components.

The temperature at which the process can be conducted is not particularly limited.

The temperature used should be below the boiling point of the composition at normal pressure (1013 mbar). Usually the process can be conducted at a temperature in the range of 5° C. to 100° C. or within a range of 10° C. to 80° C. Conducting the process under ambient temperature (e.g. about 23° C.) has been found possible as well.

The atmosphere under which the process of the invention can be conducted is not particularly limited, either.

Usually, the processes are conducted under ambient conditions. Depending on the components used, conducting the process under inert conditions can be recommended. In this respect a nitrogen or argon atmosphere could be useful.

The pressure under which the process of the invention can be conducted is not particularly limited, either. However, the process is typically conducted under ambient pressure (about 1013 mbar). The mixture should be stirred until a homogeneous dispersion or solution is obtained.

Depending on the process conditions, this can be accomplished within a few hours (e.g. at least 1 or at least 5 or at least 10 h) or a few days (e.g. at least 1 or at least 2 days). A time range within 2 to 20 h can be useful.

The pH-value of the reaction mixture depends on the components chosen.

The manner how the components are added is not particularly limited.

The composition is preferably mixed during its preparation. Mixing or dispersing of components can be accomplished using a device such as a magnetic stirrers, mechanical stirrers, dissolvers, ball mills, attritor mills or high shear equipment.

For storage, the composition described in the present text is typically packaged in a suitable packaging device.

The composition is typically provided as a one-part composition. That is, all components of the composition are present together during storage and use. No mixing of different parts of the composition is required for application.

For some applications, e.g. in order to bond dual cure or self-cure materials such as resin cements, or core build-up materials, typically a separate activator or initiator component has to be mixed with the composition.

Suitable packaging devices include vials, bottles, blisters, syringes, foil pouches, and cartridges.

If desired, the dental adhesive composition can also be provided in a single-use package.

Suitable vials are described e.g. in U.S. Pat. No. 5,996,796 (Kvitrud et al.) and WO 2011/056814 A1 (3M).

The dental adhesive composition may also be stored in a container formed by two sheets, interconnected by hot sealing and cooperating to form a compartment for receiving the liquid and a pocket for receiving a brush i.e. a blister. These kinds of devices are described e.g. in U.S. Pat. No. 6,105,761 (Peuker et al.).

The volume of the packaging device is typically in the range of 0.1 to 100 ml or 0.5 to 50 ml or 1 to 30 ml.

If the packaging device is intended for a single use only, the volume is typically in the range of 0.03 to 2 ml or 0.06 to 1 ml or 0.08 to 0.3 ml.

Described is also a kit of parts comprising the dental adhesive composition described in the present text and one or more of the following items: dental filling material, dental milling blank, dental cement, hydrofluoric acid etchant, sandblasting medium, sandblasting device instruction of use.

A dental filling material is a material which is used for restorative purposes, i.e. for filling cavities in dental tooth structure. A variety of dental filling materials is commercially available including Filtek™ Bulk Fill, Filtek™ Supreme XTE, Filtek™ Z250, Filtek™ One(3M Oral Care).

A dental milling blank is a block from which dental restorations like dental crowns and bridges can be machined. Dental milling blocks are commercially available, e.g. from 3M Oral Care (Lava™ Plus; Lava™ Esthetic).

Dental cements are used for fixing dental restorations to dental surfaces, as luting agents, cavity-lining materials and other purposes. Dental cements are typically provided as powder/liquid system or paste/paste system. A variety of dental cements is commercially available, such as RelyX™ Unicem, RelyX™ Ultimate, or RelyX™ Veneer (3M Oral Care).

The instruction of use typically contains a description of the process steps the practitioner should follow when using the dental adhesive composition described in the present text.

The composition described in the present text is in particular useful for adhesively fixing a dental restoration to a dental surface. The composition described in the present text is typically used as follows:

The composition is typically applied to the surface of a dental restorative material or a dental surface, if desired in combination with a dental cement and/or dental primer.

The dental restorative material typically has the shape of a dental crown, dental bridge, dental post, dental veneer, dental inlay, dental onlay, dental implant, dental filling, fixed or removable denture, orthodontic appliance (e.g. a bracket, ring or retainer) or part thereof.

The material of the dental restoration includes metal (e.g. gold, dental alloys), zirconia, feldspathic glass ceramic, lithium disilicate ceramic, composite, alumina, porcelain fused to metal, or composite veneered metal.

Dental restorations based on zirconia are described in WO 2012/125885 A1 (3M). Commercially available products are e.g. Lava™ Plus and Lava™ Esthetic (3M Oral Care).

Dental restorations based on feldspathic glass ceramic are described in U.S. Pat. No. 4,798,536 (Katz). Commercially available products are e.g. VitaBlocs™ Mark II (VITA Zahnfabrik).

Dental restorations based on lithium disilicate ceramic are described in US 2015/374465 (Burke et al.). Commercially available products are e.g. emax.CAD™ (Ivoclar-Vivadent).

The composition described in the present text can also be used as self-etching adhesive composition.

According to one possible use, the composition is applied to the tooth surface, typically in an amount sufficient to etch and prime dental tissue.

In this respect the following steps are generally applied:
a) applying the composition described in the present text to the surface of a tooth (enamel and/or dentin), preferably using a brush or a sponge, the surface of the tooth can be prepared, etched with an acid (e.g. phosphoric acid) or as it is,
b) optionally dispersing the composition to a thin film, preferably using a stream of air,
c) light initiated curing of the composition, the light having a wave length in range of e.g. 350 nm to 500 nm, and
d) optionally applying a dental filling composition, a dental luting cement or an orthodontic adhesive.

According to another possible use, the composition is applied to the surface of a dental restoration.

The surface of the dental restoration may have been surface treated before. Suitable surface treatments include etching (e.g. with strong acids like hydrofluoric acid) or sandblasting.

In this respect the following steps are generally applied:
a) providing a dental restoration,
b) pre-treating a part of the surface of the dental restoration,
c) applying the composition described in the present text to the pre-treated surface of the dental restoration, preferably by using a brush or a sponge,
d) optionally dispersing the composition to a thin film, preferably using a stream of air,
e) optionally light initiated curing of the composition, the light having a wave length in range of e.g. 350 nm to 500 nm, and
f) optionally applying a dental filling composite or a dental luting cement on the composition.
g) optionally shaping the filling composite and light curing it (e.g. in the case of repairing a dental restoration), or
h) optionally seating the dental restoration together with the luting cement on the site of a preparation (e.g. in the case of cementation of a restoration), and
a) optionally light curing the luting cement and the dental adhesive composition through the restoration material.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).
Methods
Shear Bond Strength (According to DIN EN ISO 29022 (2013-09))

Bovine teeth embedded in acrylic resin were ground flat to expose enamel or dentin, polished (grit 320 sandpaper) and rinsed with water.

Adhesive formulations were applied using a microbrush for 20 sec with gentle rubbing.

Solvents were removed from the adhesive using a gentle stream of pressurized air (0.3 bar) for 5 sec.

The adhesive was light cured for 10 sec using an Elipar™ S10 LED light (3M Oral Care).

Then a composite button (Filtek™ Z250, 3M Oral Care) was placed on the cured adhesive using a mold and clamp according to DIN EN ISO 29022 and cured for 20 sec using an Elipar™ S10 LED light (3M Oral Care).

Specimens were stored in water at 36° C. for 24 hours or subject to artificial aging (5000 thermal cycles, 5° C.-55° C., 30 sec dwell time).

Shear bond strength (n=10) was measured using a testing machine and a jig according to DIN EN ISO 29022 [2013-09].
Viscosity Viscosity can be measured using a Physica MCR 301 Rheometer (Anton Paar, Graz, Austria) with a cone/plate geometry CP25-1 under controlled shear rate at 23° C. The diameter is 25 mm, the cone angle 1°, and the separation between the cone tip and the plate 49 µm. The shear rate is ramped down logarithmically from $1000\ s^{-1}$ to $1\ s^{-1}$, with a total of 23 data points being collected. The integration time for each data point is 10 sec.
Radiopacity Radiopacity can be measured in accordance to DIN EN ISO 4049:2000.

Storage Stability/Homogeneity After Application (Absence of Phase Separation)

Homogeneity can be determined by placing a drop of the formulation on a laboratory glass slide, dispersing it with a gentle stream of air (about 0.3 bar pressure), and inspecting it visually. If the drop appears clear, the formulation is considered homogeneous. If the drop appears milky or cloudy, or if particles or droplets can be seen in the drop, the formulation is considered inhomogeneous and not-storage stable.

Particle Size Distribution

If desired, the particle size can be measured using a Malvern Mastersizer 2000 (Malvern Instruments, Malvern, Worcestershire, UK) light scattering instrument. The Mastersizer 2000 uses an integrated optical system to cover the range from 0.02 to 2000 μm. The mixtures to be analysed is added to the test chamber filled with isopropanol until an obscuration of approximately 8 15% is reached. No ultrasound is applied in order not to alter the particle size distributions. The raw data is processed with the instrument software using a refractive index of 1.459 and applying the Mie correction together with the Fraunhofer approximation, frequently used techniques known to the expert.

Refractive Index

If desired, the refractive index can be measured with a Kruess AR 4 D device (refractometer according to Abbe's measure principle). The refractive index is typically measured at 20.0° C. at a wavelength of 589 nm.

Materials

TABLE 1

| Name | Description |
|---|---|
| CPQ | Camphorquinone |
| HEMA | 2-Hydroxyethyl methacrylate |
| MPTS | 3-Methacryloxypropyl trimethoxysilane |
| EDMAB | Ethyl 4-dimethylaminobenzoate |
| BisGMA | Bisphenol A diglycidyl ether dimethacrylate |
| MDP | reaction products of methacrylic acid with 1,10-decanediol and phosphorous oxide (CAS 1207736-18-2) |
| A200 | fumed silica with a BET surface area of about 200 m$^2$/g, e.g. Aerosil ™ 200, available from Evonik AG |
| DMAEMA | N,N'-dimethylaminoethyl methacrylate |
| Jonol ™ (BHT) | 3,5-di-tert-butyl-4-hydroxytoluene |
| DBPGDMA | 2,2-Dibromoneopentyl glycol dimethacrylate |
| PBPMA | Pentabromophenyl methacrylate |
| BRIOLAT | 2,2-Bis[3,5-dibromo-4-(2-methacryloyloxyethoxy)phenyl]propane |
| DIBROERMA | cf. structure on page 10 above |
| OERMA | structure of DIBROERMA, but with non-brominated resorcinol moiety |

Synthesis of DIBROERMA

DIBROERMA was synthesized following a three step reaction protocol.

Due to the used reaction protocol, the reaction product DIBROERMA is a mixture of three different di-brominated species:

(3-(2,4-dibromo-5-(2-(2-(methacryloyloxy)ethoxy)ethoxy)phenoxy)propyl methacrylate,
((4,6-dibromo-1,3-phenylene)bis(oxy))bis(propane-3,1-diyl) bis(2-methylacrylate),
((((4,6-dibromo-1,3-phenyl ene)bis(oxy))bis(ethane-2,1-diyl))bis(oxy))bis(ethane-2,1-diyl) bis(2-methylacrylate))

as described in WO 2015/126865 A1 (3M) for e.g. OER-MA (inventive example 2).

Reaction Step 1: Synthesis of OER via Etherification of Resorcinol with Halogenated Alcohols OER was synthesized according to the first reaction step of inventive example 2 of WO 2015/126865 A1 (3M).

Reaction Step 2: Synthesis of DIBROER Via in situ Dibromination of OER

OER was di-brominated using two equivalents of bromination reagent in analogy to Synthesis 2010, 10, 1629-1632, Table 1, Entry 3.

Reaction Step 3: Synthesis of DIBROERMA Via Acid Catalyzed Esterification of DIBROER DIBROER was esterified with methacrylic acid to give DIBROERMA in analogy to the second reaction step of inventive example 2 of WO 2015/126865 A1 (3M).

Synthesis of BRIOLAT 2,2-Bis[3,5-dibromo-4-(2-hydroxyethoxy)phenyl]propane was esterified with methacrylic acid to give BRIOLAT in analogy to the second reaction step of inventive example 2 of WO 2015/126865 A1 (3M).

Synthesis of OERMA

OERMA can be obtained as described in inventive example 2 of WO 2015/126865 A1 (3M).

The formulations shown in Table 1 below were prepared by mixing the ingredients for 24 hours in a beaker using a magnetic stirrer bar at 23° C.

Formulations were tested for homogeneity, radiopacity, shear bond strength to bovine enamel and dentin, and viscosity (Table 2).

TABLE 2

| | I.E. 1 | C.E. 1 | C.E. 2 | C.E. 3 | C.E. 4 | C.E. 5 |
|---|---|---|---|---|---|---|
| BisGMA | — | 30.00 | — | — | — | — |
| DIBROERMA | 30.00 | — | — | — | — | — |
| BRIOLAT | — | — | — | 30.00 | — | — |
| 2,2-Dibromoneopentyl glycol dimethacrylate | — | — | — | — | 30.00 | — |
| Pentabromophenyl methacrylate | — | — | — | — | — | 30.00 |
| OERMA | — | — | 30.00 | — | — | — |
| HEMA | 19.20 | 19.20 | 19.20 | 19.20 | 19.20 | 19.20 |
| Ethanol | 12.00 | 12.00 | 12.00 | 12.00 | 12.00 | 12.00 |
| Wasser | 10.00 | 10.00 | 10.00 | 10.00 | 10.00 | 10.00 |
| MDP | 15.39 | 15.39 | 15.39 | 15.39 | 15.39 | 15.39 |
| DMAEMA | 0.71 | 0.71 | 0.71 | 0.71 | 0.71 | 0.71 |
| EDMAB | 0.90 | 0.90 | 0.90 | 0.90 | 0.90 | 0.90 |
| Camphorquinone | 1.40 | 1.40 | 1.40 | 1.40 | 1.40 | 1.40 |
| Jonol (BHT) | 0.10 | 0.10 | 0.10 | 0.10 | 0.10 | 0.10 |
| Vitrebond Copolymer | 1.00 | 1.00 | 1.00 | 1.00 | 1.00 | 1.00 |
| Aerosil A200 | 6.10 | 6.10 | 6.10 | 6.10 | 6.10 | 6.10 |
| MPTS | 3.2 | 3.2 | 3.2 | 3.2 | 3.2 | 3.2 |
| sum | 100 | 100 | 100 | 100 | 100 | 100 |
| Radiopaque | Yes | No | No | Yes | Yes | Yes |
| Homogeneous | Yes | Yes | Yes | No | No | No |
| SBS enamel selfetch [MPa] ISO 29022 | 30.0 ± 3.2 | 27.4 ± 4.2 | 24.5 ± 2.2 | 29.5 ± 3.6 | 21.2 ± 5.0 | 15.7 ± 1.2 |
| SBS dentin selfetch [MPa] ISO 29022 | 33.7 ± 4.5 | 31.5 ± 3.9 | 28.8 ± 3.1 | 26.4 ± 8.8 | 24.6 ± 2.1 | 16.0 ± 1.4 |
| viscosity 100/s, 23° C. [Pas] | 0.065 | 0.101 | 0.05 | 0.158 | 0.054 | 0.056 |

I.E. = Inventive Example;
C.E. = Comparative Example

Only the composition containing a monomer according to Component A as described in the present text (Inventive Example) was sufficiently storage stable, radiopaque, sufficiently low viscous and resulted in a high bond strength to dental surfaces.

The compositions of Comparative Examples 1 and 2 were storage stable as well, but not radiopaque.

The compositions of Comparative Examples 3-5 contained other radiopaque monomers, but were not sufficiently storage stable.

The composition of Comparative Example 5 showed a low bond strength to enamel and dentin.

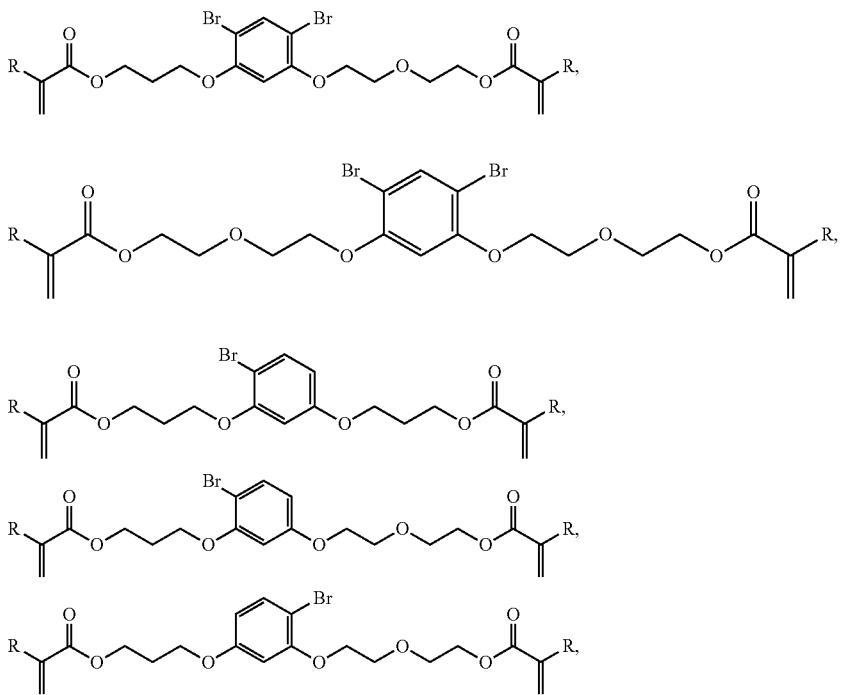

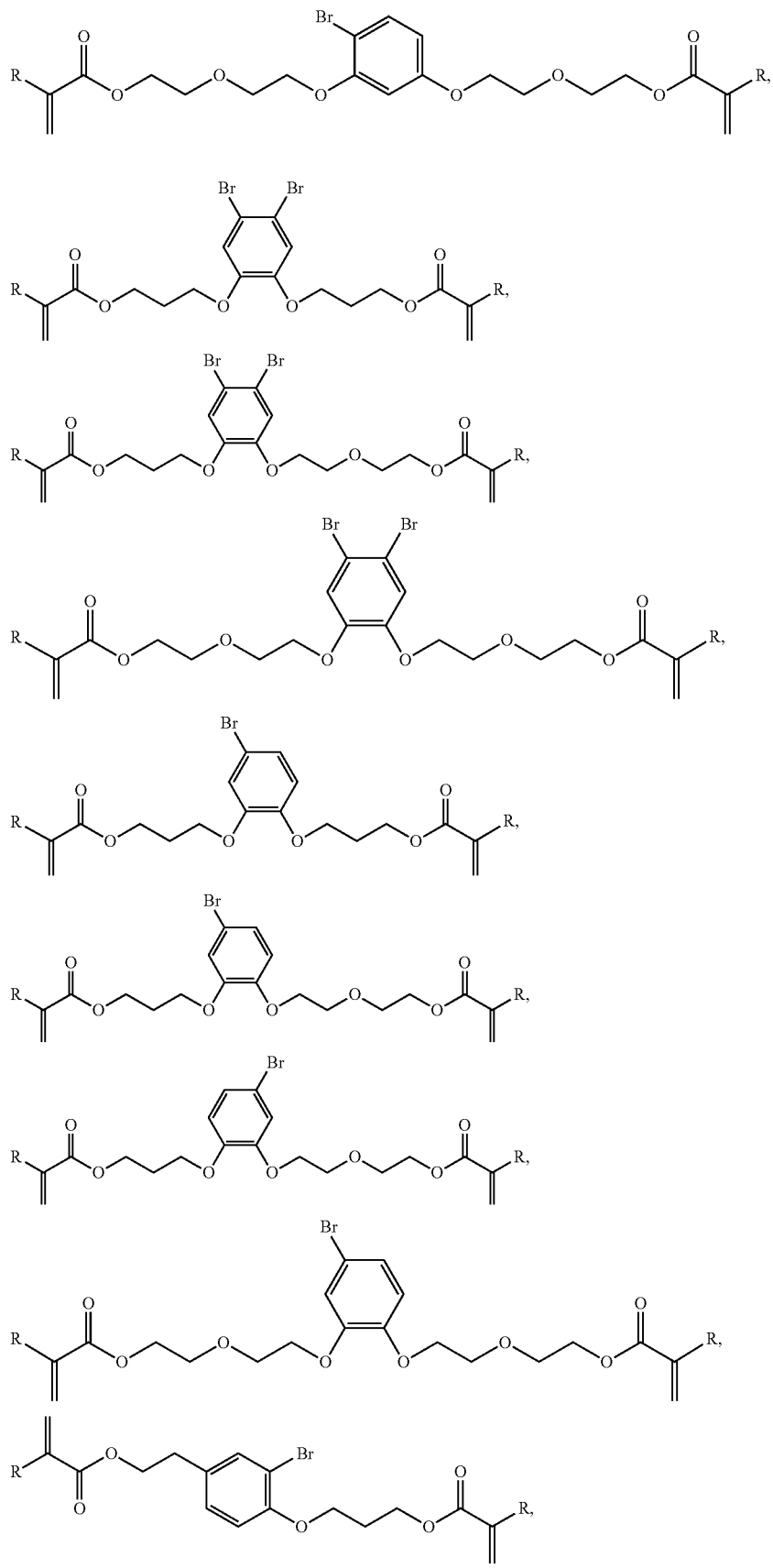

-continued
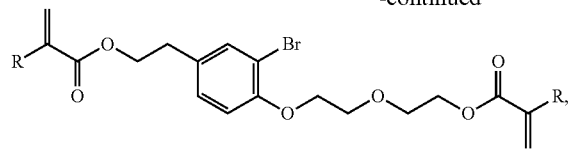
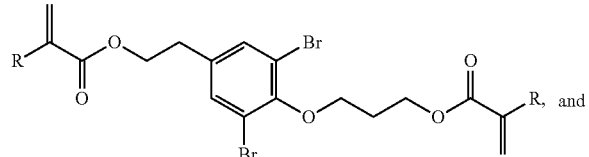
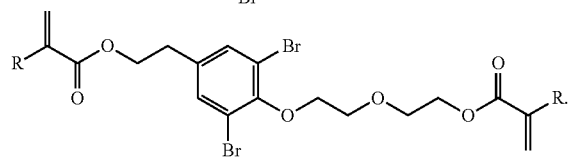
20. The dental composition of claim 19, wherein Component A is the combination of the following formulae:
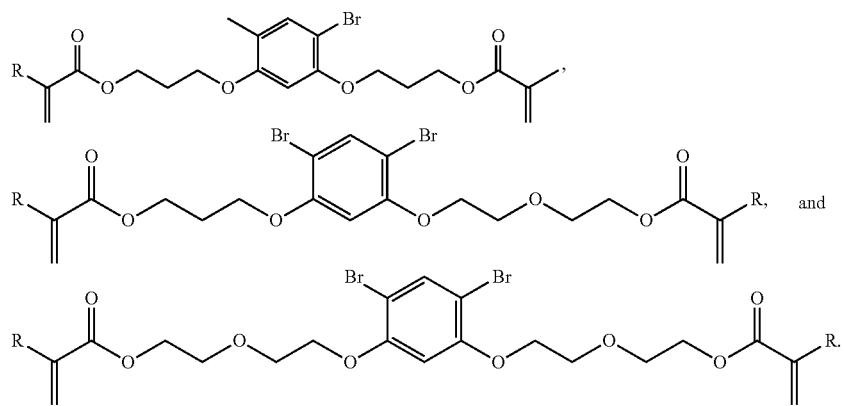

What is claimed is:

1. A dental composition comprising:
a resin matrix comprising:
cross-linkable component(s) as Component A characterized by the Formula (I):

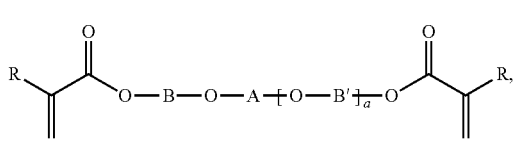

wherein:
a is an integer selected from 0 and 1,
A is selected from:

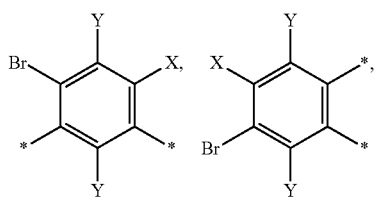

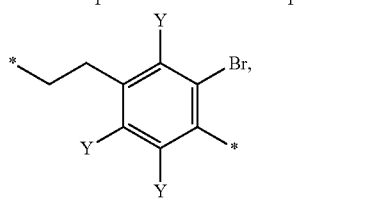

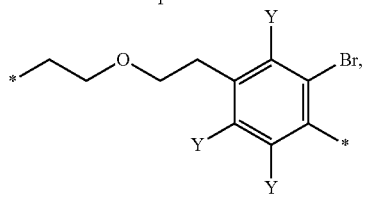

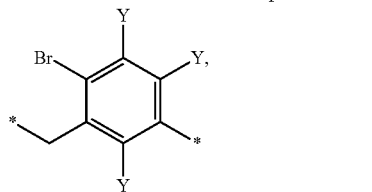

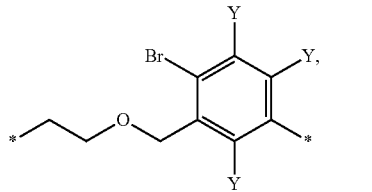

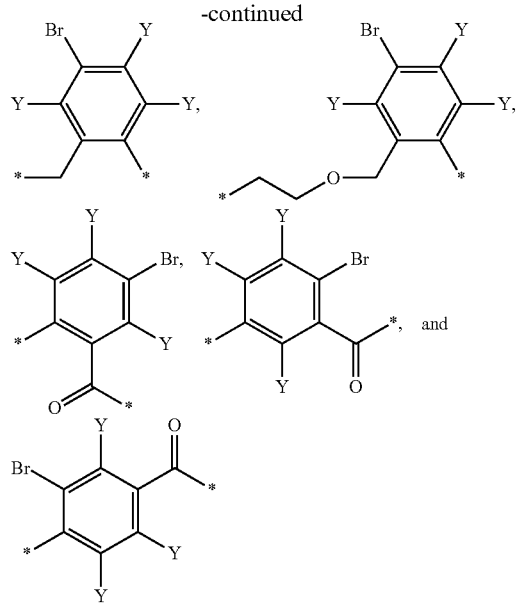

B is selected from:
*—$(CH_2)_b$—*, *—$(CH_2—CH_2—O—CH_2—CH_2)$—*, *—$(CH_2—CH_2—O—CH_2—CH_2—CH_2)$—*, *—$(CH_2—CH_2—CH_2—O—CH_2—CH_2—CH_2)$—*,

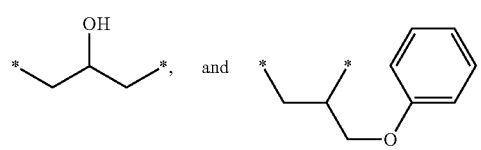

b is an integer selected from 2 to 6,
B' being selected from *—$(CH_2)_{b'}$—*, *—$(CH_2—CH_2—O—CH_2—CH_2)$—*,

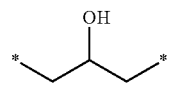

b' is an integer selected from 2 to 6,
R is H or methyl,
X is selected from H, methyl, ethyl, hexyl, tert-butyl, and Br,
Y is H and Br,
"*" representing those site(s) of a moiety of the monomer, where that moiety is bonded to another moiety of the monomer;
ethylenically unsaturated component(s) with acidic moiety as Component B; and
an initiator system comprising:
photoinitiator(s) as Component C, and
reducing agent(s) as Component D.

2. The dental composition of claim 1, for use as self-etching, self-adhesive bonding composition, restoration primer or dental sealant.

3. The dental composition of claim 1, being characterized by the following features alone or in combination:
viscosity: 0.01 to 3 Pa*s at 23° C.;
pH-value: 0.8 to 4 if determined with wet pH-sensitive paper;
shear bond strength to enamel: at least 12 MPa according to ISO 29022 (2013-09);
shear bond strength to dentin: at least 12 MPa according to ISO 29022 (2013-09);
being x-ray visible;
being storage stable.

4. The dental composition of claim 1, Component A being characterized by the following features alone or in combination:
molecular weight: 460 to 800 g/mol;
viscosity: 0.2 to 3 Pa*s at 23° C.;
refractive index: 1.52 to 1.57.

5. The dental composition of claim 1, Component A being characterized by the following formula:

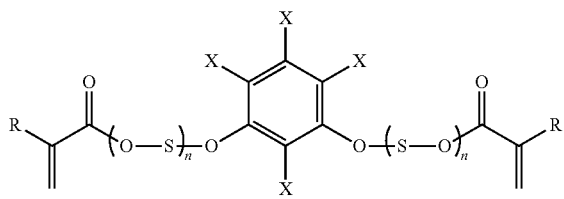

wherein:
each R is independently selected from H and $CH_3$;
each S is independently selected from a linear or branched $C_{2-3}$ alkylene group;
each X is independently selected from H and Br, wherein at least one X is Br; and
each n is independently an integer of 1 or 2.

6. The dental composition of claim 1, Component B being represented by the following formula $A_nBC_m$ wherein:
B is selected from (i) linear or branched $C_1$ to $C_{12}$ alkyl, optionally substituted with OH, (ii) $C_6$ to $C_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH,
A is an ethylenically unsaturated group,
C is an acidic group,
m is an integer selected from 1, 2, 3, 4, 5 and 6, and
n is an integer selected from 1, 2, 3, 4, 5, and 6,
wherein the acidic group comprises one or more carboxylic acid residues, phosphoric acid residues, phosphonic acid residues or sulphonic acid residues.

7. The dental composition of claim 1, comprising in addition the following components alone or in combination:
filler(s) as Component E in an amount of 0 to 25 wt. %;
solvent(s) as Component F in an amount of 0 to 50 wt. %;
water as Component G in an amount of 0 to 20 wt. %;
ethylenically unsaturated monomer(s) without an acidic moiety other than Component A as Component H in an amount of 0 to 80 wt. %;
additive(s) as Component I in an amount of 0 to 5 wt. %;
wt. % with respect to the weight of the whole composition.

8. The dental composition of claim 1, containing the components in the following amounts:
Component A: 10 to 50 wt. %,
Component B: 2 to 20 wt. %,
Component C: 0.1 to 3 wt. %,
Component D: 0.1 to 3 wt. %,
filler(s): 0 to 25 wt. %,
solvent(s): 0 to 50 wt. %,
water: 0 to 20 wt. %,
ethylenically unsaturated monomer(s) without an acidic moiety other than Component A:
0 to 40 wt. %,
additive(s): 0 to 10 wt. %,
wt. % with respect to the weight of the whole composition.

9. The dental composition of claim 1, not comprising the following components alone or in combination:
aldehydes in an amount of more than 1 wt. %;
solvent(s) with a boiling point above 150° C. in an amount of more than 2 wt. %;
bisphenol A-glycidyl methacrylate in an amount of more than 5 or 10 wt. %;
coloured dyes or pigments which are not photobleachable in an amount of more than 1 wt. %;
fillers with an average particle size larger than 50 μm in an amount or more than 1 wt. %;
wt. % with respect to the weight of the whole composition.

10. The dental composition of claim 5,
wherein Component A is present in an amount of 20 to 50 wt. %,
Component B represented by the formula:

$A_nBC_m$ wherein:
B is selected from (i) linear or branched $C_1$ to $C_{12}$ alkyl, optionally substituted with OH, (ii) $C_6$ to $C_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH,
A is an ethylenically unsaturated group,
C is an acidic group,
m is an integer selected from 1, 2, 3, 4, 5 and 6,
n is an integer selected from 1, 2, 3, 4, 5 and 6,
wherein the acidic group comprises one or more phosphoric acid residues and mixtures thereof, and
wherein Component B is present in an amount of 5 to 20 wt. %,
Component C:
being selected from components comprising an alpha di-keto moiety, an anthraquinone moiety, a thioxanthone moiety or benzoin moiety and mixtures thereof, and
being present in an amount of 0.1 to 3 wt. %,
Component D:
being selected from secondary and tertiary amines and mixtures thereof, and
being present in an amount of 0.1 to 3 wt. %,
filler(s):
being selected from submicron silica particles thereof, and
being present in an amount of 1 to 20 wt. %, solvent(s):
being selected from alcohols, ketones, esters, ethers and mixtures thereof, and
being present in an amount of 1 to 30 wt. %,
water:
being present in an amount of 1 to 20 wt. %,
ethylenically unsaturated monomer(s) without an acidic moiety other than Component A:
being selected from non-brominated, ethylenically unsaturated component(s) without acidic moiety(s) and mixtures thereof and
being present in an amount of 10 to 40 wt. %,
additive(s):
being selected from inhibitors, retarders, stabilizers, dyes, fluoride release agents, wetting agents, antioxidants and mixtures thereof and
being present in an amount of 1 to 10 wt. %,
wt. % with respect to the weight of the whole composition.

11. The dental composition of claim 1, for use in a process comprising the step of applying the dental composition to a dental surface and/or adhesively fixing a dental restoration to a dental surface.

12. A process of treating a surface of a dental restoration, the process comprising:
applying a dental composition of claim 1 to the surface of a dental restoration.

13. A kit of parts comprising:
a dental composition of claim 1, and
either of the following parts alone or in combination
dental filling material;
dental milling blank;
dental cement;
hydrofluoric acid etchant;
sandblasting medium;
sandblasting device;
a dental filling material.

14. The dental composition of claim 1, Component A being characterized by the following formula:

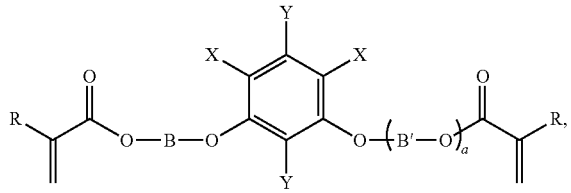

wherein each X is H or Br, wherein at least one X is Br.

15. The dental composition of claim 1, wherein Component A is selected from:

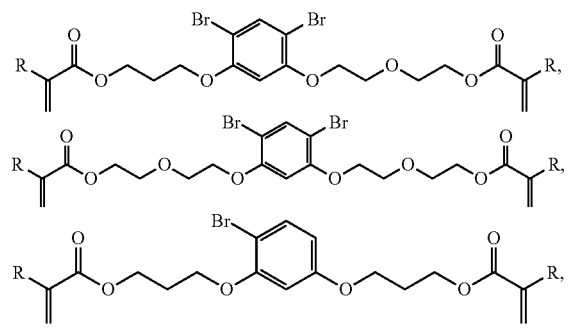

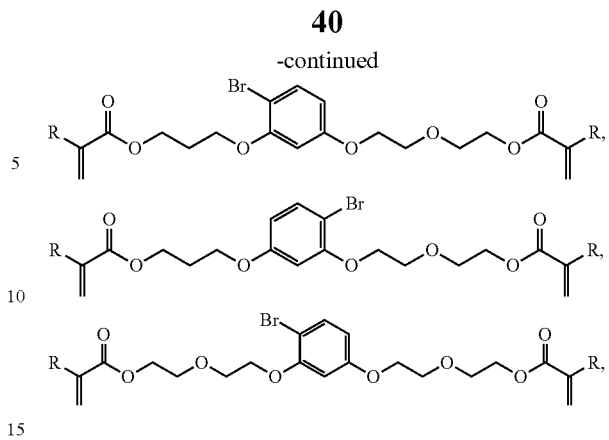

and a combination thereof.

16. The dental composition of claim 1, wherein Component A is selected from:

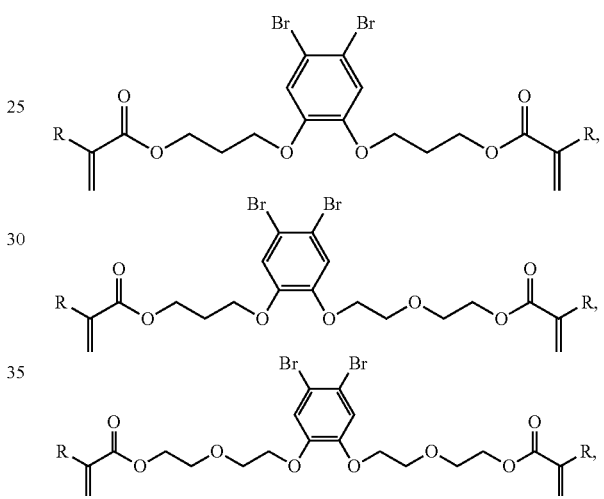

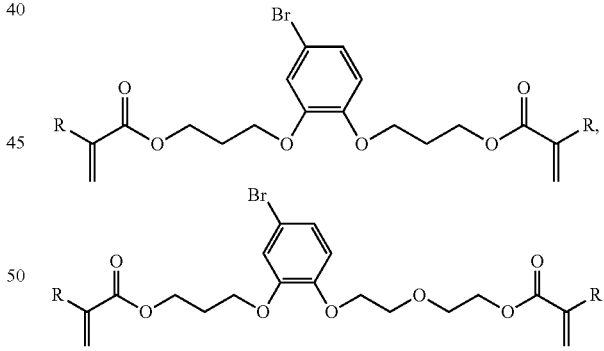

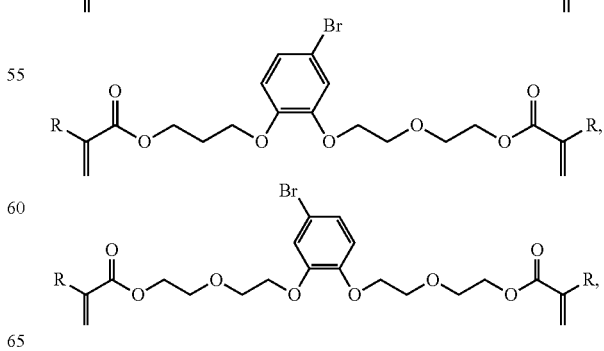

and a combination thereof.

17. The dental composition of claim 1, wherein Component A is selected from:

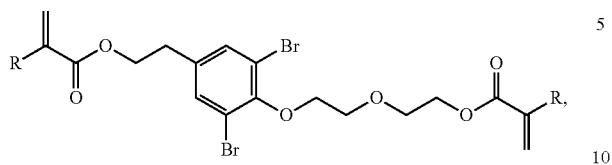

and a combination thereof.

18. The dental composition of claim 1, wherein Component A is a combination of:

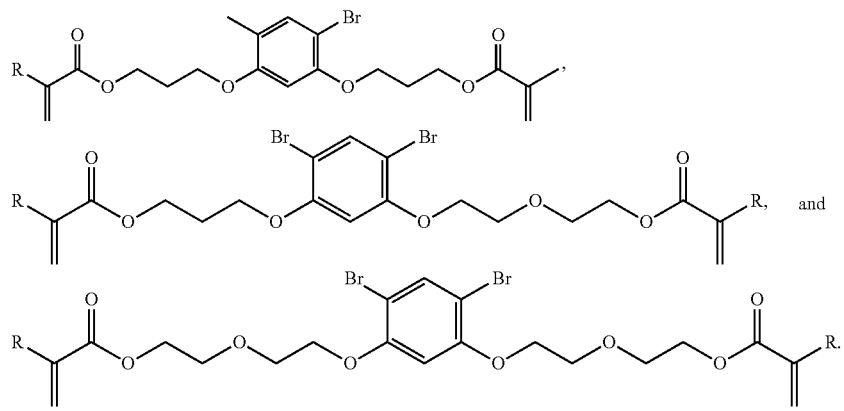

19. A dental composition comprising:
a resin matrix comprising:
  cross-linkable component(s) as Component A;
  ethylenically unsaturated component(s) with acidic moiety as Component B; and
an initiator system comprising:
  photoinitiator(s) as Component C, and
  reducing agent(s) as Component D,
wherein Component A is characterized by one or more of the following formulae: